United States Patent
Dupau et al.

(10) Patent No.: US 9,714,263 B2
(45) Date of Patent: Jul. 25, 2017

(54) SELECTIVE HYDROGENATION OF ALDEHYDES WITH RU/BIDENTATE LIGANDS COMPLEXES

(71) Applicant: FIRMENICH SA, Geneva (CH)

(72) Inventors: Philippe Dupau, Geneva (CH); Lucia Bonomo, Geneva (CH); Laurent Kermorvan, Geneva (CH)

(73) Assignee: Firmenich SA, Geneva (CH)

( * ) Notice: Subject to any disclaimer, the term of this patent is extended or adjusted under 35 U.S.C. 154(b) by 31 days.

(21) Appl. No.: 14/777,502

(22) PCT Filed: Mar. 6, 2014

(86) PCT No.: PCT/EP2014/054337
§ 371 (c)(1),
(2) Date: Sep. 15, 2015

(87) PCT Pub. No.: WO2014/139854
PCT Pub. Date: Sep. 18, 2014

(65) Prior Publication Data
US 2016/0039853 A1  Feb. 11, 2016

(30) Foreign Application Priority Data

Mar. 15, 2013 (EP) .................................... 13159479

(51) Int. Cl.
*C07F 15/00* (2006.01)
*C07C 29/14* (2006.01)
*C07C 29/157* (2006.01)

(52) U.S. Cl.
CPC .......... *C07F 15/0046* (2013.01); *C07C 29/14* (2013.01); *C07C 29/157* (2013.01)

(58) Field of Classification Search
CPC .... C07F 15/0046; C07C 29/157; C07C 29/14
USPC ................................... 556/18; 568/838, 881
See application file for complete search history.

(56) References Cited

U.S. PATENT DOCUMENTS 6,720,439 B1    4/2004  Ohkuma et al.

FOREIGN PATENT DOCUMENTS

| EP | 901997 | 7/2002 |
|----|--------|--------|
| EP | 1813621 | 6/2011 |
| EP | 1741693 | 8/2011 |
| WO | WO0174829 | 10/2001 |
| WO | WO0222526 | 3/2002 |
| WO | WO0240155 | 5/2002 |
| WO | WO2009055912 | 5/2009 |
| WO | WO2010038209 | 4/2010 |

OTHER PUBLICATIONS

International Search Report and Written Opinion, application PCT/EP2014/054337, mailed Jul. 21, 2014.

*Primary Examiner* — Porfirio Nazario Gonzalez
(74) *Attorney, Agent, or Firm* — Winston & Strawn LLP

(57) ABSTRACT

The present invention relates to processes for the reduction by hydrogenation, using molecular $H_2$, of a $C_5$-$C_{20}$ substrate containing one or two aldehydes functional groups into the corresponding alcohols or diol, characterized in that said process is carried out in the presence of —at least one catalyst or pre-catalyst in the form of a ruthenium complex having a coordination sphere of the $N_1P_3O_2$, wherein the coordinating atom N and one coordinating atom P are provided by a first bidentate ligand, and the two other coordinating atoms $P_2$ are provided by a second bidentate ligand and the coordinating atoms $O_2$ are provided by two non-linear carboxylate ligands; and —optionally of an acidic additive.

10 Claims, No Drawings

SELECTIVE HYDROGENATION OF ALDEHYDES WITH RU/BIDENTATE LIGANDS COMPLEXES

TECHNICAL FIELD

The present invention relates to the field of catalytic hydrogenation and to the use of ruthenium complexes having a coordination sphere of the $N_1P_3O_2$, wherein the coordinating atoms $O_2$ are provided by two carboxylate ligands, in hydrogenation processes for the reduction of aldehydes into the corresponding alcohols.

PRIOR ART

Reduction of an aldehyde into the corresponding alcohol is one of the fundamental reactions in organic chemistry, and is used in a large number of chemical processes. The most convenient manner to achieve such reduction is to use a hydrogenation (using $H_2$) process.

Several types of catalysts performing hydrogenation of carbonyl groups have been described in the last years and the most relevant ones are Ru complexes having a $P_2N_2$ coordination sphere, and more precisely a $P_2N_2Cl_2$ coordination sphere, which reduces indistinctly an aldehyde or a ketone and does require the presence of a base in the medium (e.g. see EP 0901997, EP 1813621, WO09/055912, WO02/022526 or WO02/40155). However as mentioned said systems all require the presence of a strong base and this limitation hampers such catalytic systems to be industrially used with base sensitive substrates like most of aldehydes.

Only few catalytic systems for the aimed reduction have been reported to be active in the absence of a base (and generally displaying low reactivity) and none in the presence of a weak acid. For instance EP 1741693 or U.S. Pat. No. 6,720,439 recites the use of Ru complexes having a $P_2N_2HY$ coordination sphere (Y being an anion like Cl), however such system is described as being active only for the reduction of ketones. Alternatively, WO02/022526 mentions that $[Ru(PN)_2(CH_3(CH_2)_{0-1}COO)_2]$ can be effective for the base-free reduction of base insensitive aromatic ketones.

The patent application WO2001/74829 reports the use of a cyclophane-diphosphine ruthenium complex of formula [(cyclophane-diphosphine)(diamines)RuX$_2$], wherein X is halide or carboxylate. However such document mentions only CF$_3$COO as a carboxylate anionic ligand, i.e. a carboxylate of different nature compared to the one of the invention, and reports the use of those complexes only in the reduction of ketones, while in the present invention the catalysts are displaying efficient reactivity only in the reduction of aldehydes.

The patent application WO2010/038209 reports the use of bidentate phosphi-phosphine oxide ruthenium complex of formula [(phosphi-phosphine oxide)(diamines)RuX$_2$], but this complex requires in general a base and is not selective toward ketones.

The patent application EP1366004 reports the use of Ru complexes having a $P_3NY_2$ coordination sphere (Y being an anion like Cl or AcO) but these complexes require in general a base and are not selective toward ketones.

Therefore, aldehydes being generally sensitive to basic conditions, there is still a need for efficient hydrogenation processes allowing the base-free selective reduction of aldehyde in the presence of olefins, and also displaying selectivity towards ketones.

To the best of our knowledge, the prior art does not report or suggest that the presently claimed catalysts (having branched carboxylates as coordinated anions) are indeed active in the free-base reduction of aldehydes and that are selective toward ketones and other functional groups such as olefins for example.

DESCRIPTION OF THE INVENTION

In order to overcome the problems aforementioned, the present invention relates to processes for the reduction by hydrogenation, using molecular $H_2$, of a $C_5$-$C_{20}$ substrate containing one or two aldehydes functional groups into the corresponding alcohol or diol, characterized in that said process is carried out in the presence of at least one catalyst or pre-catalyst in the form of a ruthenium complex having a coordination sphere of the $N_1P_3O_2$, wherein the coordinating atom N and one coordinating atom P are provided by a first bidentate ligand, and the two other coordinating atoms $P_2$ are provided by a second bidentate ligand and the coordinating atoms $O_2$ are provided by two non-linear carboxylate ligands; and optionally an acidic additive.

As well understood by a person skilled in the art, by "bidentate" it is understood that said ligand coordinates the Ru metal with two atoms (e.g. two P or one P and one N).

The terms "catalyst or pre-catalyst" are also referred to with the general term "complex".

According to a particular embodiment of the invention, the substrate can be a compound of formula (I)

wherein $R^a$ represents a $C_4$-$C_{19}$ linear, branched or cyclic alkyl, alkenyl or alkadienyl group optionally comprising an aromatic ring and optionally comprising one, two or three functional groups selected among ketone, ether, carbon-carbon double or triple bond and carboxylic groups.

It is important to point out that the substrate may contain also functional groups such as ketones, indeed one of the advantages of said process is that the hydrogenation is particularly selective and it is possible to selectively hydrogenate the aldehyde group without reducing a ketone group which may be present in the starting substrate.

The corresponding alcohols (I-a) of said substrate (I), are of formula

wherein $R^a$ is defined as in formula (I).

It is understood that by "a linear, branched or cyclic alkyl, alkenyl or alkadienyl group" it is meant that said $R^a$ can be in the form of, e.g., a linear alkyl group or can also be in the form of a mixture of said type of groups, e.g. a specific $R^a$ may comprise a branched alkenyl, a (poly)cyclic alkyl and a linear alkyl moiety, unless a specific limitation to only one type is mentioned. Similarly, in all the below embodiments of the invention, when a group is mentioned as being an alkenyl or alkadienyl it is meant that said group comprises one or two carbon-carbon double bond which can be conjugated or not with the aldehyde group or between them, in the case of alkadienyl. Similarly, in all the below embodiments of the invention, when a group is mentioned as being in the form of more than one type of topology (e.g. linear, cyclic or branched) and/or unsaturation (e.g. alkyl or alkenyl) it is meant also a group which may comprise moieties having any one of said topologies or unsaturations, as explained above. Similarly, in all the below embodiments of the invention, when a group is mentioned as being in the form of one type of unsaturation, (e.g. alkyl), it is meant that said group can be in any type of topology (e.g. linear, cyclic or branched) or having several moieties with various topologies.

According to any one of the invention's embodiments, the substrate is an aldehyde that will provide an alcohol that is useful in the pharmaceutical, agrochemical or perfumery industry as final product or as an intermediate. Particularly preferred substrate is an aldehyde that will provide an alcohol which is useful in the perfumery industry as final product or as an intermediate.

According to any one of the invention's embodiments, the substrate is a $C_5$-$C_{20}$ compound of formula (I), and in particular one may cite those wherein $R^a$ represents:

a $C_4$-$C_{19}$ group of formula

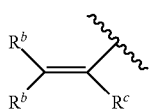

(a)

wherein $R^c$ represents a hydrogen atom or a $C_{1-3}$ alkyl group and each $R^b$, independently from each other, represents a hydrogen atom, a linear, branched or cyclic alkyl or alkenyl group optionally comprising an aromatic ring and optionally comprising one or two functional groups selected among ketone, ether, carbon-carbon triple bond and carboxylic groups; two of said $R^b$ and $R^c$ groups may be bonded together to form a $C_{5-7}$ ring optionally comprising one or two functional groups selected among ketone and ether groups, provided that at least one $R^b$ group is not a hydrogen atom;

a $C_4$-$C_{19}$ linear, branched or cyclic deconjugated alkenyl or alkadienyl group optionally comprising an aromatic ring and optionally comprising one or two functional groups selected among ketone, ether, carbon-carbon triple bond and carboxylic groups;

a $C_4$-$C_{19}$ linear, branched or cyclic alkyl group optionally comprising an aromatic ring and optionally comprising one or two functional groups selected among ketone, ether, carbon-carbon triple bond and carboxylic groups.

According to any one of the invention's embodiments, the substrate is a $C_5$-$C_{16}$ compound of formula (I) wherein $R^a$ represents:

a $C_4$-$C_{15}$ group of formula

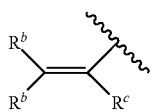

(a)

wherein $R^c$ represents a hydrogen atom or a $C_{1-3}$ alkyl group and each $R^b$, independently from each other, represents a linear, branched or cyclic alkyl or alkenyl group optionally comprising one functional group selected among ketone, ether and carboxylic groups;

a $C_4$-$C_{15}$ linear, branched or cyclic deconjugated alkenyl or alkadienyl group optionally comprising an aromatic ring and optionally comprising one functional group selected among ketone, ether and carboxylic groups;

a $C_4$-$C_{15}$ linear, branched or cyclic alkyl group optionally comprising an aromatic ring and optionally comprising one functional group selected among ketone, ether and carboxylic groups.

It is understood that by "deconjugated alkenyl or alkadienyl group" it is meant that the carbon-carbon double bonds are not conjugated with the aldehyde functional group.

Non-limiting examples of substrates of formula (I) are the following:

$C_{5-16}$ aldehydes such as:
2,3-dimethylbut-2-enal, cyclohex-3-enecarbaldehyde, 3-methylhex-2-enal, 6-oxoheptanal, (Z)-oct-5-enal, 3,7-trimethyl-octa-2,6-dienal, 3,7-dimethyloct-6-enal, (2,2-dimethyl-3-(2-oxopropyl)cyclopropyl)acetaldehyde, (3-acetyl-2,2-dimethylcyclobutyl)acetaldehyde, 3,6,7-trimethyl-octa-2,6-dienal, 3,6,7-trimethyloct-6-enal, undec-10-enal, endo 2-(3-(2-oxopropyl)bicyclo[2.2.1]heptan-2-yl)acetaldehyde, (E)-4-methyl-5-(p-tolyl)pent-4-enal, 2,2-dimethyl-6-methylene-7-(3-oxobutyl)cycloheptane carbaldehyde, 4-(3,3-dimethyl-2-(3-oxobutyl)cyclobutyl)pent-4-enal; said compounds are all known to be highly base-sensitive substrates even at room temperature.

In the present invention, contrary to almost all the examples in the prior art, the presence of a base is avoided. This is an advantage, since it allows significant increases in yields for the production of alcohols from base-sensitive aldehydes. Therefore, according to any one of the invention's embodiments, the substrate is a base-sensitive compound.

According to any one of the invention's embodiments, the ruthenium complex can be of the general formula

[Ru(PP)(PN)(RCOO)$_2$]   (1)

wherein PP represents a $C_6$-$C_{50}$ bidentate ligand wherein the coordinating groups are two phosphino groups;
PN represents a $C_2$-$C_{20}$ bidentate ligand wherein the coordinating groups are one amino group and one phosphino group; and
each R represents, simultaneously or independently, a $C_2$-$C_{12}$ hydrocarbon group branched or cyclic in the α and/or β position, and said hydrocarbon group is optionally comprising one to five heteroatom selected amongst halogen, oxygen and nitrogen atoms.

According to any one of the invention's embodiments, in formula (1), each R represents, simultaneously or independently:
a $C_{2-12}$ alkyl group branched or cyclic in the α and/or β position
optionally substituted by one phenyl group optionally substituted by one to five halogen atoms and/or by $C_{1-4}$ alkyl or alkoxyl groups; and
optionally comprising one OH, amino or ether functional group;

or a phenyl group optionally substituted by one to three, or five, halogen atoms and/or by $C_{1-4}$ alkyl or alkoxyl groups and/or by nitro groups.

According to a particular embodiment of the formula (1), said R group represents a branched $C_{3-10}$ alkyl group comprising in the α position a tertiary or quaternary carbon atom and/or in the β position a quaternary carbon atom and also optionally comprising one OH, one ether functional group or one phenyl group, the phenyl group being optionally substituted by one or two halogen atoms and/or by $C_{1-4}$ alkyl or alkoxyl groups;

a $C_2$ alkyl group comprising in the α position one OH or one ether functional group; or a phenyl group optionally substituted by one, two or three halogen atoms and/or by $C_{1-4}$ alkyl or alkoxyl groups and/or nitro groups.

According to a particular embodiment of the formula (1), said R group represents a branched $C_{3-10}$ alkyl group comprising in the α position a tertiary or quaternary carbon atom and/or in the β position a quaternary carbon atom; or a phenyl group optionally substituted by one, two or three halogen atoms and/or by $C_{1-4}$ alkyl or alkoxyl groups and/or nitro groups.

For the sake of clarity, by the expression "α position" it is meant the usual meaning in the art, i.e. the carbon atom directly bound to the COO moiety of the group RCOO. Similarly by the expression "β position" it is meant a carbon atom directly bound to the α position. For the sake of clarity, by the expression "group branched or cyclic" it is meant a group which is not linear, i.e. a cyclohexyl, a iso-propyl, or $ClCH_2$ but not $CH_2CH_3$ or $CCl_3$, and it is also clear that the branching may be due to one or several carbon atoms or an optional functional group, which may be part of a cycle or not.

As non-limiting examples of suitable RCOO group of (I), one may cite the isobutyrate, pivalate, ′Bu-acetate, 2-Et-hexanoate, cyclohexanecarboxylate, picolinate, cinnamate, benzoate, 4-Me-benzoate, 4-OMe-benzoate, 3,5-dichloro-benzoate, 2,4-dichloro-benzoate, isovalerate, adamantate or sec-butyrate.

According to any one of the embodiments of the present invention, the bidentate ligand (PP) can be a compound of formula

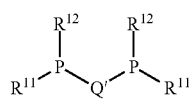

(C)

wherein $R^{11}$ and $R^{12}$, when taken separately, represent, simultaneously or independently, a $C_{3-6}$ branched or cyclic alkyl group or a $C_{6-10}$ aromatic group optionally substituted; and Q′ represents a group of formula

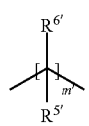

(i′)

wherein m′ is 1, 2, 3 or 4 and $R^{5'}$ and $R^{6'}$ represent, simultaneously or independently, a hydrogen atom, a $C_{1-6}$ linear or branched alkyl group or a $C_{6-10}$ aromatic group optionally substituted; two distinct $R^{6'}$ and/or $R^{5'}$ groups, taken together, may form a $C_3$ to $C_8$ saturated or unsaturated ring optionally substituted, including the atoms to which said $R^{6'}$ and/or $R^{5'}$ groups are bonded, and optionally containing one or two additional nitrogen or oxygen atoms; or a $C_{10}$-$C_{16}$ metallocenediyl, a 2,2′-diphenyl, a 1,1′-binaphthalene-2,2′-diyl, a benzenediyl, a naphthalenediyl, 2,3-bicyclo[2:2:1]hept-5-enediyl, 4,6-phenoxazinediyl, 4,5-(9,9-dimethyl)-xanthenediyl, or bis(phen-2-yl) ether group optionally substituted.

As mentioned above, according to a particular embodiment of the invention, by "aromatic group or ring" for (PP) it is also meant a phenyl or naphthyl derivative.

As mentioned above, in said ligand (C) the atoms which may coordinate the Ru atom are the P atoms of the $PR^{11}R^{12}$ groups. Therefore, it is also understood that whenever said $R^{5'}$, $R^{6'}$, $R^{11}$, $R^{12}$, Q′ or any other group comprises heteroatoms such as N or O, said heteroatoms are not coordinating.

Possible substituents of $R^{5'}$, $R^{6'}$, $R^{11}$ and $R^{12}$ are one to five halogen atoms (in particular when said substituents are on aromatic moieties), or one, two or three i) $C_{1-6}$ linear or branched alkyl, alkoxy, groups or halo- or perhalo-hydrocarbon, amine groups, ii) $COOR^h$ wherein $R^h$ is a $C_{1-6}$ linear, branched or cyclic alkyl group, iii) $NO_2$ group, or iv) a benzyl group or a fused or non-fused phenyl group, said group being optionally substituted by one, two or three halogen atoms, $C_{1-8}$ alkyl, alkoxy, amino, nitro, ester, sulfonate or halo- or perhalo-hydrocarbon groups. By "halo- or perhalo-hydrocarbon" it is meant groups such as $CF_3$ or $CClH_2$ for instance.

For the sake of clarity, and as mentioned above, in any one of the embodiments of the present invention, whenever two groups of formula (C) are taken together to form a cycle or ring, said cycle or ring can be a mono or bi-cyclic group.

According to any one of the invention's embodiments of said bidentate PP ligand, $R^{11}$ and $R^{12}$, when taken separately, represent, simultaneously or independently, a $C_{3-6}$ cyclic alkyl group or a $C_{6-10}$ aromatic group, or preferably a phenyl group, optionally substituted.

According to any one of the invention's embodiments of said bidentate PP ligand, $R^{11}$ and $R^{12}$ represent each, simultaneously or independently, a $C_{4-6}$ branched or cyclic alkyl group or a phenyl group optionally substituted.

According to any one of the invention's embodiments of said bidentate PP ligand, Q′ represents a group of formula

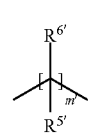

(i′)

wherein m′ is 1, 2, 3 or 4 and $R^{5'}$ and $R^{6'}$ represent, simultaneously or independently, a hydrogen atom, a $C_{1-4}$ linear or branched alkyl group or a $C_{6-10}$ aromatic group, or preferably a phenyl group, optionally substituted; two distinct $R^{6'}$ and/or $R^{5'}$ groups, taken together, may form a $C_{4-6}$ saturated or unsaturated ring optionally substituted, including the atoms to which said $R^{6'}$ and/or $R^{5'}$ groups are bonded; or a $C_{10}$-$C_{16}$ metallocenediyl, a 2,2'-diphenyl; a benzenediyl, a naphthalenediyl, a 1,1'-binaphthalene-2,2'-diyl, 2,3-bicyclo[2:2:1]hept-5-enediyl, 4,6-phenoxazinediyl, 4,5-(9,9-dimethyl)-xanthenediyl or bis(phen-2-yl)ether group optionally substituted.

According to any one of the invention's embodiments of said bidentate PP ligand, Q' may represent a linear $C_{1-5}$ alkanediyl radical, a 1,2- or 1,1'-$C_{10-12}$ metallocenediyl, a 2,2'-diphenyl, a 1,2-benzenediyl, a 1,1'-binaphthalene-2,2'-diyl, or a 1,8- or 1,2-naphthalenediyl or a 4,5-(9,9-dimethyl)-xanthenediyl group optionally substituted.

According to a particular embodiment of the invention, said PP ligand is a compound of formula (C) wherein $R^{11}$ and $R^{12}$ represent, simultaneously or independently, a $C_{4-6}$ branched or cyclic alkyl group or a phenyl group optionally substituted; and Q' represents a $C_1$-$C_4$ alkanediyl radical optionally substituted, a $C_{10}$-$C_{12}$ ferrocenediyl, a 2,2'-diphenyl, a 1,1'-binaphthalene-2,2'-diyl, a 1,2-benzenediyl or a naphthalenediyl group.

According to any one of the invention's embodiments of said bidentate PP ligand, said ligand is a compound wherein one, two or three of the Q', $R^{11}$ and $R^{12}$ groups are satured groups (i.e. alkyl or alkanediyl groups). In particular Q' represents a $C_1$-$C_4$ alkanediyl radical optionally substituted and/or $R^{11}$ and $R^{12}$ a branched or cyclic alkyl group.

Possible substituents of said $R^{11}$ or $R^{12}$ are as described above for $R^1$ to $R^6$. Possible substituents of said Q' are as described above for Q.

As non limiting examples of PP ligands, one can cite the ones in the following Scheme (B):

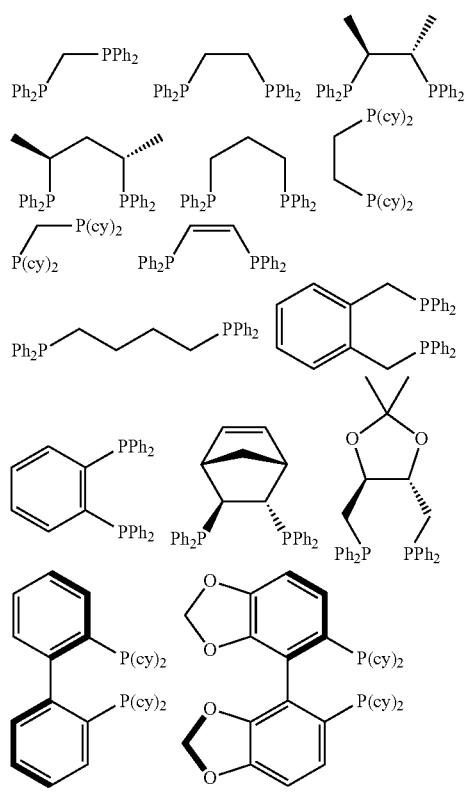
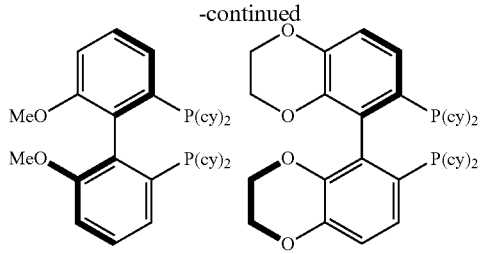
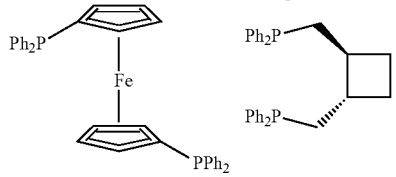
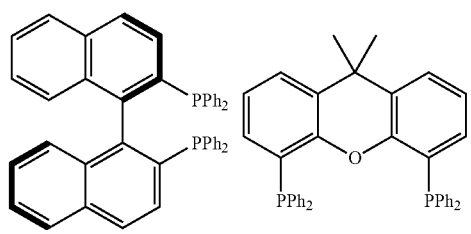
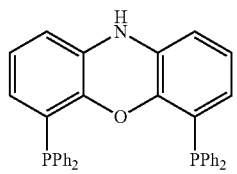
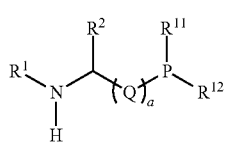

said compounds being in an optically active form or in a racemic form, if applicable, and wherein Ph represents a phenyl group and cy represents a $C_{5-6}$ cycloalkyl group. It is also understood that in the above diphosphines, one may replace cy group by a Ph group or vice versa.

According to any one of the invention's embodiments, the bidentate PN ligand is a compound of formula (B)

$$R^1\text{—}N(\text{H})\text{—}C(R^2)(R^{11})\text{—}(Q)_a\text{—}P(R^{12})$$

wherein a represent 0 or 1, $R^{11}$ and $R^{12}$ being defined as for PP herein above;

$R^1$ represent, simultaneously or independently, a hydrogen atom or a $C_{1-6}$ linear, branched or cyclic alkyl group or a benzyl group optionally substituted;

$R^2$ represents a hydrogen atom, a $C_{1-6}$ linear, branched alkyl group or a $C_{6-10}$ aromatic group optionally substituted; $R^1$ and $R^2$, taken together, may form a saturated heterocycle containing 5 to 8 atoms and including the atoms to which said $R^1$ and $R^2$ are bonded, and optionally containing one additional nitrogen or oxygen atom; and Q represents
a group of formula

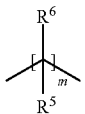
(i)

wherein m is 1, 2 or 3, and

R⁵ and R⁶ represent, simultaneously or independently, a hydrogen atom, a $C_{1-6}$ linear, branched or cyclic alkyl or, a $C_{6-10}$ aromatic group optionally substituted; two distinct R⁶ and/or R⁵ groups, taken together, may form a $C_{3-8}$ saturated ring optionally substituted, including the atoms to which said R⁶ and/or R⁵, groups are bonded, and optionally containing one or two additional nitrogen or oxygen atoms; or a $C_{10}$-$C_{16}$ metallocenediyl group, a benzenediyl group, or a naphthalenediyl group, said group being optionally substituted.

According to an embodiment, by "aromatic group or ring" it is meant a phenyl or naphthyl group.

As mentioned above, in said ligand (B) the atoms which may coordinate the Ru atom are one N atom bearing the R¹ groups and one P atom bearing the R¹¹/R¹² groups. Therefore, it is also understood that whenever said R¹, R², R⁵, R⁶ or any other group comprises heteroatoms such as N or O, said heteroatoms are not coordinating.

Possible optional substituents of R¹, R², R⁵, R⁶ or Q are one, two, three or four groups selected amongst i) halogen atoms (in particular when said substituents are on aromatic moieties), ii) $C_{1-6}$ alkoxy, alkyl, alkenyl groups, or iii) a benzyl group or a fused or non-fused phenyl group, said group being optionally substituted by one, two or three halogen atoms, $C_{1-8}$ alkyl, alkoxy, amino, nitro, ester, sulfonate or halo- or perhalo-hydrocarbon groups.

For the sake of clarity, and as mentioned above, in any one of the embodiments of the present invention, whenever two groups of formula (B) are taken together to form a cycle or ring, said cycle or ring can be a mono or bi-cyclic group.

According to any one of the invention's embodiments of said bidentate PN ligand, R¹ represents a hydrogen atom or a $C_{1-4}$ linear or branched alkyl group. In particular R¹ is a hydrogen atom.

According to any one of the invention's embodiments of said bidentate PN ligand, R² represents a hydrogen atom, a $C_{1-4}$ linear or branched alkyl group or a phenyl group optionally substituted; R¹ and R², taken together, may form a saturated heterocycle containing 5 or 6 atoms and including the atoms to which said R¹ and R² are bonded and optionally containing one additional oxygen atom.

According to any one of the invention's embodiments of said bidentate PN ligand, R² represents a hydrogen atom, a $C_{1-4}$ linear or branched alkyl group.

According to any one of the invention's embodiments of said bidentate PN ligand, said Q represents Q represents
a group of formula

(i)

wherein m is 1 or 2, and

R⁵ and R⁶ represent, simultaneously or independently, a hydrogen atom, a $C_{1-4}$ linear, branched or cyclic alkyl or a phenyl group optionally substituted; or a benzenediyl group, or a naphthalenediyl group, said group being optionally substituted.

According to any one of the invention's embodiments of said bidentate PN ligand, said Q can be a group of formula (i) wherein m is 1 or 2, R⁵ is a hydrogen atom and R⁶ is as defined above. In particular each R⁵ and R⁶ may represent a hydrogen atom.

According to a particular embodiment of the invention, alternatively said Q can be a benzenediyl group.

According to any one of the invention's embodiments of said bidentate PN ligand, is represented by formula

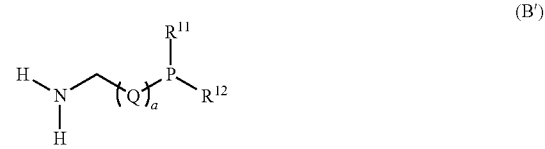
(B')

wherein a represents 0 or 1, R¹¹ and R¹² being defined as for PP herein above; and Q represents
a group of formula

(i)

wherein m is 1 or 2, and

R⁶ represents, simultaneously or independently, a hydrogen atom, a $C_{1-4}$ linear or branched alkyl group; or a benzenediyl group optionally substituted.

According to any one of the invention's embodiments of said bidentate PN ligand, the possible substituents of R¹, R², R⁵, or R⁶ or Q of formulae (B) or (B') are one or two i) halogen atoms or ii) $C_{1-5}$ alkyl or alkoxy groups.

According to any one of the above-mentioned embodiments, the PN ligand is of formula (B').

As non limiting examples of PN ligands one can cite the ones in the following Scheme (A):

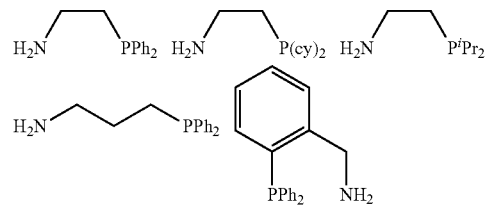

said compounds being in an optically active form or in a racemic form, if applicable, and wherein Ph represents a phenyl group and cy represents a $C_{5-6}$ cycloalkyl group. It is also understood that in the above aminophosphines, one may replace cy group by a Ph group or vice versa.

The ligands described above can be obtained by applying standard general methods which are well known in the state of the art and by the person skilled in the art. Many of said ligands PN or PP are even commercially available.

The complexes of formula (1) are generally prepared and isolated prior to their use in the process as exemplified in the Examples herein below but can also be generated directly in situ from the precursor [(PP)Ru(RCOO)$_2$] using one equivalent of PN ligand respect to ruthenium. In addition, said complexes (1) can also be generated in situ from the known aminophosphine diphosphine ruthenium complex derivatives (PP)(PN)Ru(X)(Y), such as di-acetate, di-propionate, di-alkoxyde (di-isopropoxyde for example), hydridoborohydrido, cationic monoacetate or dicationic (or a mix of those) complexes by adding an excess of an acid RCOOH wherein R has the meaning provided in formula (1). The said complexes (1) can also be generated in situ from the known chlorinated ruthenium complex derivatives (PP)(PN)Ru(Cl)(Y) such as dichloride or cationic monochloride complexes by adding an excess of an acid RCOOH wherein R has the meaning provided in formula (1), optionally in the presence of a stoechiometric amount of a silver salt (AgOCOCH$_3$, AgBF$_4$, AgPF$_6$, AgOSO$_2$CF$_3$ for example) with respect to chloride atoms.

The invention complexes of formula (1) are novel, to the best of our knowledge. Therefore such complex (1) is also an object of the present invention.

As previously mentioned, the processes may comprise the addition of an acidic additive. Said additive has the astonishing effect of increasing the speed and sometimes also the yield of the reaction.

Said acidic additive may be selected amongst the weak protic acids, i.e. compounds capable of releasing protons and having a pK$_a$ comprised between 2 and 11. In particular said acidic additive can be selected amongst:
- a carboxylic acid of formula RCOOH, wherein R is as defined above in formula (1); and
- phenol (C$_6$H$_5$OH) and a phenol substituted by one or two, or up to five, halogen atoms and/or C$_{1-4}$ alkyl or alkoxyl groups and/or nitro groups and/or carboalkoxy groups.

According to any embodiments of the present invention, said acidic additive can be selected amongst:
- a carboxylic acid of formula RCOOH, wherein R is as defined above in formula (1); or
- phenol (C$_6$H$_5$OH) and a phenol substituted by one to five halogen atoms and/or by one or two C$_{1-4}$ alkyl or alkoxyl groups and/or nitro groups and/or carboalkoxy groups.

According to any embodiments of the present invention, said carboxylic acid has a pK$_a$ comprised between 3 and 5.5. Similarly, according to any embodiments of the present invention, said substituted or unsubstituted phenol has a pK$_a$ comprised between 5 and 10.5.

As non limiting examples of said acidic additive, one may cite the following: diphenylphosphonic acid, hexylboronic acid, 4-NO$_2$-phenol, 4-carbomethoxyphenol, 4-OMe-phenol, pentafluorophenol, isobutyric acid, sec-butyric acid, pivalic acid, $^t$Bu-acetic acid, 2-Et-hexanoic acid, cyclohexanecarboxylatic acid, picolinic acid, cinnamic acid, benzoic acid, 2,4,6-trimethyl-benzoic acid, 4-Me-benzoic acid, 4-NO$_2$-benzoic acid, 4-OMe-benzoic acid, 3,5-diCl-benzoic acid, 2,4-diCl-benzoic acid, 1-adamantane carboxylic acid or isovaleric acid.

The said acidic additive can be added as such into the reaction medium or, as in the case of the carboxylic acids, can be generated in situ, e.g. by adding a carboxylic anhydride and optionally an alcohol.

As previously mentioned, the processes of the invention consist in the hydrogenation of a substrate using a ruthenium complex in the absence of a base. A typical process implies the mixture of the substrate with the ruthenium complex, and optionally a solvent and an acidic additive, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 1 ppm to 10000 ppm relative to the amount of substrate. Preferably, the complex concentration will be comprised between 10 ppm to 2000 ppm. It goes without saying that the optimum concentration of complex will depend, as the person skilled in the art knows, on the nature of the latter, on the nature and quality of the substrate, on the nature of the solvent used if any, on the reaction temperature and on the pressure of H$_2$ used during the process, as well as the desired time of reaction.

Useful quantities of acidic additive, added to the reaction mixture, may be comprised in a relatively large range. One can cite, as non-limiting examples, ranges between 1 to 10000 molar equivalents, relative to the complex of formula (1), preferably 10 to 2000 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include C$_{6-10}$ aromatic solvents such as toluene or xylene; C$_{5-12}$ hydrocarbon solvents such as hexane or cyclohexane; C$_{4-8}$ ethers such as tetrahydrofuran or MTBE; C$_{4-10}$ esters such as ethyl acetate; C$_{1-2}$ chlorinated hydrocarbon, such as dichloromethane; C$_{2-6}$ primary or secondary alcohols, such as isopropanol or ethanol; C$_{2-6}$ polar solvents such as DMF, acetonitrile, DMSO, acetone; or mixtures thereof. In particular said solvent can be an apolar aprotic solvent such as an aromatic solvent or a hydrocarbon solvent. The choice of the solvent is a function of the nature of the complex and the substrate, and the person skilled in the art is well able to select the solvent most convenient in each case to optimize the hydrogenation reaction.

In the hydrogenation process of the invention, the reaction can be carried out at a H$_2$ pressure comprised between $10^5$ Pa and $80 \times 10^5$ Pa (1 to 100 bars) or even more if desired. Again, a person skilled in the art is well able to adjust the pressure as a function of the catalyst load and of the dilution of the substrate in the solvent. As examples, one can cite typical pressures of 1 to $50 \times 10^5$ Pa (5 to 50 bars).

The temperature at which the hydrogenation can be carried out is comprised between 0° C. and 200° C., more preferably in the range of between 50° C. and 150° C. Of course, a person skilled in the art is also able to select the preferred temperature as a function of the melting and boiling point of the starting and final products as well as the desired time of reaction or conversion.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in stainless steel autoclave. $H_2$ gas (99.99990%) was used as received. All substrates and solvents were distilled from appropriate drying agents under Ar. NMR spectra were recorded on a Bruker AM-400 ($^1$H at 400.1 MHz, $^{13}$C at 100.6 MHz, and $^{31}$P at 161.9 MHz) spectrometer and normally measured at 300 K, in $CD_2Cl_2$ unless indicated otherwise. Chemical shifts are listed in ppm.

Example 1

The invention's complexes were generally synthesized according to a two steps procedure going through the corresponding [Ru(PP)(RCOO)$_2$]ruthenium(diphosphine)(biscarboxylate) derivatives, those being isolated or not.

Two Step Procedure:

A) The [Ru(diene)(RCOO)$_2$] (in general [Ru(COD)(RCOO)$_2$], see the application PCT/IB2011/052108) precursor was loaded into a schlenck tube. It was then purged with three vacuum-nitrogen cycles. Degazed xylene (technical quality can be used) was then added to generally afford a suspention. Diphosphine (1 eq./Ru) was then added to the stirred suspension that was then heated to reflux (140-144° C.) under nitrogen for several hours (duration depending on nature of diphosphine ligand). After cooling down and xylene removal, degassed MeOH was generally added for product precipitation (nature of solvent used can obviously depends on the nature of both diphosphine and carboxylate ligands). It was then filtered under nitrogen, washed several times with degassed MeOH (again, nature of solvent used can obviously depends on the nature of both diphosphine and carboxylate ligands) and then dried under vacuum to afford the desired corresponding [Ru(diphosphine)(RCOO)$_2$] complex in generally more than 90 mol. % yields.

B) The obtained [Ru(diphosphine)(RCOO)$_2$] precursor was loaded into a schlenck tube. It was then purged with three vacuum-nitrogen cycles. Degazed THF was then added followed by aminophosphine ligand (1 eq./Ru). Reaction mixture was then heated to reflux (66° C.) under nitrogen for several hours (duration depending on nature of the aminophosphine ligand. After cooling down and THF removal under vacuum, degassed 30/50 petroleum ether was generally added for product precipitation (nature of solvent used can obviously depends on the nature of aminopohsphine, diphosphine and carboxylate ligands). It was then filtered under nitrogen and washed several times with degassed 30/50 petroleum ether (again, nature of solvent used can obviously depends on the nature of aminophosphine, diphosphine and carboxylate ligands). After drying under vacuum, desired [Ru(PP)(PN)(RCOO)$_2$] complex was obtained in more than 60 mol. % yield as cis or trans isomer (carboxylate in cis or trans position) or cis/trans isomers mixture, both stereochemistry and yields mainly depending on the nature of the ligands used.

[(2-(diphenylphosphino)ethanamine)[1,4-bis(diphenylphosphino)butane]Ru(pivalate)$_2$]

$^{31}$P NMR: 26.19 (dd, J=300.0 and 30.9, 1P trans isomer), 35.75 (t, 30.9, 1P trans isomer), 46.92 (dd, J=300 and 30.9, 1P trans isomer).

$^{13}$C NMR (trans isomer): 21.15 (d, J=4.4, CH$_2$), 24.63 (broad s, CH$_2$), 24.72 (d, J=18.4, CH$_2$), 27.07 (d, J=24.0, CH$_2$), 28.84 (s, CH$_3$), 33.28 (dd, J=22.8 and 3.5, CH$_2$), 40.11 (s, C), 40.66 (t, J=6.2, CH$_2$), 127.26 (d, J=8.8, CH), 127.41 (d, J=8.2, CH), 128.13 (d, J=8.4, CH), 129.01 (broad s, CH), 129.18 (s, CH), 133.74 (broad s, CH), 134.96 (broad s, CH), 138.0 (broad s, C), 140.90 (broad s, C), 188.30 (broad s, C).

[(2-(diphenylphosphino)ethanamine)[1,3-bis(diphenylphosphino)propane]Ru(pivalate)$_2$]

$^{31}$P NMR: 25.30 (dd, J=29.0 and 43.5, 1P trans isomer), 27.98 (dd, J=300.0 and 43.5, 1P trans isomer), 42.33 (dd, =300.0 and 29.0, 1P trans isomer).

$^{13}$C NMR (trans isomer): 19.37 (d, J=2.9, CH$_2$), 26.89 (dd, J=26.4 and 3.6, CH$_2$), 27.96 (d, J=23.7, CH$_2$), 28.93 (s, CH$_3$), 32.57 (dd, J=21.2 and 4.0, CH$_2$), 40.11 (s, C), 40.67 (t, J=7.0, CH$_2$), 127.40 (d, J=9.0, CH), 127.91 (d, J=7.8, CH), 128.33 (d, J=8.6, CH), 129.02 (broad s, CH), 129.13 (d, J=1.6, CH), 129.27 (broad s, CH), 133.40 (d, J=9.8, CH), 134.44 (d, J=8.8, CH), 136.27 (d, J=3.2, C), 136.63 (d, J=3.4, C), 188.4 (broad s, C).

[(2-(diphenylphosphino)ethanamine)[1,2-bis(diphenylphosphino)ethane]Ru(pivalate)$_2$]

$^{31}$P NMR: 44.46 (dd, J=318.0 and 27.8, 1P trans isomer), 58.75 (dd, J=318.0 and 20.6, 1P trans isomer), 59.39 (dd, =27.8 and 20.6, 1P trans isomer).

$^{13}$C NMR (trans isomer): 28.15 (dd, J=28.3 and 13.1, CH$_2$), 28.74 (s, CH$_3$), 30.26 (ddd, J=27.2, 15.9 and 4.0, CH$_2$), 33.26 (dd, J=21.2 and 3.3, CH$_2$), 39.77 (s, C), 41.71 (dd, J=7.5 and 4.5, CH$_2$), 127.80 (d, J=8.8, CH), 128.13 (d, J=8.7, CH), 128.31 (d, J=8.6, CH), 129.03 (d, J=1.5, CH), 129.15 (d, J=1.8, CH), 129.42 (d, J=1.8, CH), 133.08 (d, J=9.5, CH), 133.56 (d, J=9.9, CH), 133.91 (d, J=10.0, CH), 135.84 (dd, J=33.6 and 4.2, C), 136.49 (d, J=33.8 and 3.0, C), 141.40 (d, J=36.8, C), 187.44 (s, C).

[(2-(diphenylphosphino)ethanamine)[1,1-bis(diphenylphosphino)methane]Ru(pivalate)$_2$]

$^{31}$P NMR: −3.91 (dd, J=334.8 and 43.4, 1P trans isomer), 9.18 (dd, J=43.4 and 30.0, 1P trans isomer), 53.54 (dd, J=334.8 and 30.0, 1P trans isomer).

$^{13}$C NMR: 28.12 (CH$_3$), 31.69 (dd, J=21.4 and 3.0, CH$_2$), 39.7 (s, C), 41.99 (t, J=6.6, CH$_2$), 46.69 (t, J=17.5, CH$_2$), 128.13 (d, J=9.5, CH), 128.27 (d, J=9.0, CH), 129.35 (t, J=2.5, CH), 129.64 (d, J=2.5, CH), 133.15 (d, J=12.0, CH), 133.50 (d, J=10.6, CH), 133.86 (d, J=11.6, CH), 135.43 (dd, J=21.7 and 2.5, C), 135.95 (dt, J=25.8 and 5.0, C), 137.37 (dd, J=33.5 and 5.8, C), 187.94 (s, C).

[(2-(diphenylphosphino)ethanamine)[9,9-dimethyl-4,5-bis(diphenylphosphino) xanthene]Ru(pivalate)$_2$]

$^{31}$P NMR: 23.84 (dd, J=28.0 and 24.0, 1P isomer 1), 37.59 (dd, J=37.0 and 28.0, 1P isomer 1), 47.31 (broad t, J=25.0, 1P isomer 2), 49.82 (dd, J=37.0 and 23.0, 1P isomer 1), 51.26 (dd, J=32.8 and 24.5, 1P isomer 2), 58.12 (d, J=30.0, 2P isomer 3), 66.68 (dd, J=32.8 and 26.0, 1P isomer 2), 74.77 (t, 30.0, 1P isomer 3).

[(2-(diphenylphosphino)ethanamine)[2,2'-bis(diphenylphosphino)-1,1'-binaphthalene]Ru(pivalate)$_2$]

$^{31}$P NMR: 27.61 (d, J=31.8, 1P isomer 1), 29.56 (d, J=31.6, 1P isomer 2), 31.62 (d, J=27.9, 1P isomer 2), 33.57

(d, J=27.9, 1P isomer 1), 38.00 (dd, J=31.6 and 27.9, 1P isomer 2), 40.50 (dd, J=31.8 and 27.9, 1P isomer 1).

[(2-(diphenylphosphino)ethanamine)[(oxybis(2,1-phenylene))bis(diphenylphosphine)]Ru(pivalate)$_2$]

$^{31}$P NMR: 34.97 (dd, J=29.2 and 24.2, 1P isomer 1), 40.54 (dd, J=36.3 and 29.2, 1P isomer 1), 45.01 (braod s, 1P isomer 2), 47.65 (dd, J=36.3 and 24.2, 1P isomer 1), 50.64 (d, J=32.0, 1P isomer 2), 73.28 (d, J=32.0, 1P isomer 2).

[(2-(diphenylphosphino)ethanamine)[1,1'-Bis(diphenylphosphino)ferrocene]Ru(pivalate)$_2$]

$^{31}$P NMR: 45.62 (dd, J=34.6 and 28.6, 1P isomer 1), 48.25 (dd, J=28.6 and 24.5, 1P isomer 1), 50.56 (d, J=31.7, 1P isomer 2), 55.39 (dd, J=34.6 and 24.5, 1P isomer 1), 64.23 (broad s, 1P isomer 2), 73.30 (d, J=32.4, 1P isomer 2).

[(2-(di-tert-butylphosphino)ethanamine)[1,4-bis(diphenylphosphino)butane]Ru(pivalate)$_2$]

$^{31}$P NMR: 17.14 (broad s, 1P isomer 1), 22.21 (broad s, 1P isomer 2), 49.96 (d, J=41.2, 1P isomer 2), 59.41 (very broad s, 2P isomer 1), 66.34 (d, J=41.2, 1P isomer 2).

[(2-(diphenylphosphino)phenyl)methanamine)[9,9-dimethyl-4,5-bis(diphenylphosphino)xanthene]Ru(pivalate)$_2$]

$^{31}$P NMR: 27.00 (dd; J=11.8 and 7.2, 1P isomer 1), 40.54 (t, J=16.0, 1P isomer 2), 44.89 (dd, J=37.6 and 7.2, 1P isomer 1), 53.72 (d, J=31.0, 2P isomer 3), 55.54 (dd, J=38.8 and 16.0, 1P isomer 2), 66.28 (dd, J=37.6 and 11.8, 1P isomer 1), 74.84 (t, J=31.0, 1P isomer 3), 75.99 (dd, J=38.8 and 16.0, 1P isomer 2).

[(3-(diphenylphosphino)propan-1-amine)[9,9-dimethyl-4,5-bis(diphenylphosphino) xanthene]Ru(pivalate)$_2$]

$^{31}$P NMR: 55.22 (d, J=30.4, 2P isomer 1), 56.41 (d, J=29.8, 2P isomer 2), 57.20 (t, J=30.4, 1P isomer 1), 61.98 (t, J=29.8, 1P isomer 2).

[(2-(diphenylphosphino)ethanamine)[1,2-bis(diphenylphosphino)ethane]Ru(benzoate)$_2$]

$^{31}$P NMR: 43.75 (dd, J=309.8 and 25.6, 1P trans isomer), 59.50 (dd, J=25.6 and 20.9, 1P trans isomer), 61.36 (dd, J=310.7 and 20.9, 1P trans isomer).
$^{13}$C NMR (trans isomer): 28.36 (dd, J=28.8 and 12.6, CH$_2$), 29.36 (ddd, J=28.0, 15.7 and 4.1, CH$_2$), 33.85 (dd, J=21.6 and 3.2, CH$_2$), 42.08 (dd, J=8.2 and 4.7, CH$_2$), 127.35 (s, CH), 128.00 (d, J=8.9, CH), 128.23 (d, J=8.5, CH), 128.29 (d, J=8.5, CH), 129.02 (s, CH), 129.29 (d, J=1.8, CH), 129.34 (d, J=1.7, CH), 129.57 (d, J=1.5, CH), 129.65 (s, CH), 133.07 (d, J=9.5, CH), 133.52 (d, J=9.9, CH), 133.72 (d, J=10.1, CH), 135.17 (dd, J=34.3 and 3.6, C), 135.95 (dd, J=33.8 and 2.8, C), 137.72 (s, C), 140.60 (d, J=37.1, C), 176.67 (s, C).

[(2-(diphenylphosphino)ethanamine)[1,2-bis(diphenylphosphino)ethane]Ru(1-adamantanecarboxylate)$_2$]

$^{31}$P NMR: 44.08 (dd, J=318.1 and 27.9, 1P trans isomer), 58.69 (dd, J=318.1 and 20.6, 1P trans isomer), 59.22 (dd, J=27.9 and 20.6, 1P trans isomer).
$^{13}$C NMR (trans isomer): 28.17 (dd, J=28.5 and 12.6, CH$_2$), 29.19 (s, CH), 30.41 (ddd, J=27.2, 15.5 and 4.2, CH$_2$), 33.06 (dd, J=20.8 and 3.5, CH$_2$), 42.08 (dd, J=4.8 and 4.1, CH$_2$), 37.36 (s, CH$_2$), 40.38 (s, CH$_2$), 41.47 (t, J=6.7, CH$_2$), 41.93 (s, C), 127.74 (d, J=8.9, CH), 128.24 (t, J=8.6, CH), 129.08 (d, J=1.4, CH), 129.18 (d, J=3.0, CH), 129.43 (d, J=1.6, CH), 133.23 (d, J=9.5, CH), 133.67 (d, J=10.0, CH), 134.08 (d, J=9.8, CH), 135.96 (dd, J=33.4 and 3.6, C), 136.23 (dd, J=33.6 and 3.2, C), 141.49 (d, J=37.0, C), 187.03 (s, C).

[(2-(diphenylphosphino)ethanamine)[9,9-dimethyl-4,5-bis(diphenylphosphino) xanthene]Ru(1-adamantanecarboxylate)$_2$]

$^{31}$P NMR: 23.97 (dd, 27.6 and 24.0, 1P isomer 1), 37.57 (dd, J=38.1 and 27.6, 1P isomer 1), 47.12 (broad t, J=25.5, 1P isomer 2), 49.55 (dd, J=38.1 and 24.0, 1P isomer 1), 51.24 (dd, J=32.4 and 24.5, 1P isomer 2), 58.11 (d, J=30.2, 2P isomer 3), 66.68 (dd, J=32.4 and 26.5, 1P isomer 2), 74.76 (t, 30.2, 1P isomer 3).

[(2-(diphenylphosphino)ethanamine)[1,2-bis(diphenylphosphino)ethane]Ru(isobutyrate)$_2$]

$^{31}$P NMR: 43.41 (dd, J=313.5 and 24.1, 1P trans isomer), 60.18 (dd, J=24.1 and 21.6, 1P trans isomer), 61.42 (dd, J=313.5 and 21.6, 1P trans isomer).
$^{13}$C NMR (trans isomer): 20.00 (s, CH$_3$), 20.41 (s, CH$_3$), 28.31 (dd, J=28.5 and 12.6, CH$_2$), 30.74 (ddd, J=26.39, 15.8 and 4.0, CH$_2$), 33.33 (dd, J=20.8 and 3.1, CH$_2$), 37.82 (s, CH), 41.72 (dd, J=8.2 and 4.4, CH$_2$), 127.71 (d, J=8.7, CH), 128.00 (d, J=8.6, CH), 128.33 (d, J=8.5, CH), 129.10 (d, J=1.5, CH), 129.17 (d, J=1.4, CH), 129.54 (d, J=1.4, CH), 133.03 (d, J=9.6, CH), 133.43 (d, J=10.2, CH), 133.74 (d, J=9.6, CH), 135.58 (dd, J=31.0 and 2.8, C), 135.61 (d, J=33.7, C), 136.10 (dd, J=33.8 and 3.0, C), 141.35 (d, J=37.9, C), 186.25 (s, C).

[(2-(diphenylphosphino)ethanamine)[1,2-bis(diphenylphosphino)ethane]Ru(3,3-dimethylbutyrate)$_2$]

$^{31}$P NMR: 43.06 (dd, J=317.2 and 26.1, 1P trans isomer), 60.38 (dd, J=26.1 and 20.8, 1P trans isomer), 62.28 (dd, J=317.2 and 20.8, 1P trans isomer).
$^{13}$C NMR (trans isomer): 28.49 (dd, J=29.3 and 12.2, CH$_2$), 29.97 (s, CH$_3$), 30.21 (s, C), 30.76 (ddd, J=27.6, 15.8 and 3.6, CH$_2$), 32.96 (dd, J=21.0 and 3.3, CH$_2$), 41.49 (dd, J=9.2 and 4.8, CH$_2$), 52.73 (s, CH$_2$), 127.54 (d, J=8.9, CH), 127.99 (d, J=8.6, CH), 128.34 (d, J=8.5, CH), 129.15 (broad s, CH), 129.45 (d, J=1.6, CH), 133.13 (d, J=9.8, CH), 133.57 (d, J=10.1, CH), 133.81 (d, J=9.7, CH), 135.38 (dd, J=33.0 and 3.0, C), 135.76 (dd, J=33.2 and 3.7, C), 141.34 (d, J=37.6, C), 181.61 (s, C).

[(2-(diphenylphosphino)ethanamine)[1,2-bis(diphenylphosphino)ethane]Ru(2,2-dimethylbutyrate)$_2$]

$^{31}$P NMR: 44.11 (dd, J=317.6 and 26.1, 1P trans isomer), 57.59 (dd, J=317.6 and 20.6, 1P trans isomer), 59.23 (dd, J=26.1 and 20.6, 1P trans isomer).
$^{13}$C NMR (trans isomer): 8.97 (s, CH$_3$), 24.73 (s, CH$_3$), 25.18 (s, CH$_3$), 28.27 (dd, J=28.4 and 13.1, CH$_2$), 30.40 (ddd, J=27.1, 14.9 and 4.0, CH$_2$), 32.97 (dd, J=21.2 and 3.4, CH$_2$), 33.35 (s, CH$_2$), 41.57 (dd, J=7.8 and 4.7, CH$_2$), 43.00 (s, C), 127.78 (d, J=8.8, CH), 128.10 (d, J=8.5, CH), 128.29 (d, J=8.6, CH), 129.02 (d, J=1.4, CH), 129.15 (d, J=1.8, CH), 129.34 (d, J=1.5, CH), 133.14 (d, J=9.5, CH), 133.59 (d, J=10.2, CH), 134.00 (d, J=9.8, CH), 136.09 (dd, J=33.7 and 3.5, C), 136.24 (dd, J=33.6 and 3.2, C), 141.65 (d, J=37.1, C), 187.29. (s, C).

[(2-(diphenylphosphino)ethanamine][1,2-bis(diphenylphosphino)ethane]Ru(cyclohexanecarboxylate)$_2$]

$^{31}$P NMR: 43.37 (dd, J=315.4 and 25.2, 1P trans isomer), 60.12 (dd, J=25.2 and 21.5, 1P trans isomer), 61.78 (dd, J=315.4 and 21.5, 1P trans isomer).

$^{13}$C NMR (trans isomer): 26.54 (s, CH$_2$), 26.66 (s, CH$_2$), 26.87 (s, CH$_2$), 28.37 (dd, J=29.1 and 12.4, CH$_2$), 30.19 (s, CH$_2$), 30.70 (s, CH$_2$), 30.81 (ddd, J=32.0, 15.9 and 4.2, CH$_2$), 33.32 (dd, J=20.8 and 3.2, CH$_2$), 41.66 (dd, J=7.7 and 4.6, CH$_2$), 48.18 (s, CH), 127.63 (d, J=8.8, CH), 128.00 (d, J=8.7, CH), 128.27 (d, J=8.7, CH), 129.08 (d, J=1.4, CH), 129.17 (d, J=1.3, CH), 129.53 (d, J=1.4, CH), 133.08 (d, J=9.5, CH), 133.48 (d, J=10.2, CH), 133.84 (d, J=9.8, CH), 135.65 (dd, J=34.0 and 3.2, C), 135.98 (dd, J=33.8 and 3.0, C), 141.29 (d, J=37.5, C), 185.48. (s, C).

[(2-(diphenylphosphino)ethanamine][1,2-bis(diphenylphosphino)ethane]Ru(cyclopropanecarboxylate)$_2$]

$^{31}$P NMR: 43.16 (dd, J=313.6 and 25.2, 1P trans isomer), 60.67 (dd, J=25.2 and 22.0, 1P trans isomer), 62.64 (dd, J=313.6 and 22.0, 1P trans isomer).

$^{13}$C NMR (trans isomer): 5.99 (s, CH$_2$), 16.38 (s, CH), 28.22 (dd, J=29.3 and 12.3, CH$_2$), 30.57 (ddd, J=32.3, 16.1 and 4.3, CH$_2$), 33.64 (dd, J=21.0 and 3.3, CH$_2$), 41.86 (dd, J=8.8 and 5.0, CH$_2$), 127.61 (d, J=8.9, CH), 127.91 (d, J=8.8, CH), 128.29 (d, J=8.6, CH), 129.15 (d, J=1.2, CH), 129.48 (d, J=1.8, CH), 133.07 (d, J=9.6, CH), 133.59 (d, J=8.4, CH), 133.68 (d, J=8.4, CH), 135.25 (dd, J=33.2 and 3.8, C), 136.16 (dd, J=33.6 and 3.1, C), 141.11 (d, J=37.6, C), 183.09. (s, C).

Example 2

Catalytic Hydrogenation of Aldehydes Using the Invention's Process: Comparative Example with Various Prior Art Catalysts

Influence of Nature of Ruthenium Precursor on Catalytic Activity in 3,7-Dimethyloct-6-Enal (Citronellal) Selective Hydrogenation General Procedure:

3,7-dimethyloct-6-enal (15.4 g, 0.1 mol), isopropanol (15.4 g, 100 wt. %), ruthenium complex (0.01 mmol., 0.01 mol. %) and, whenever required tBuOK as additive (112 mg, 1 mmol., 1 mol. %, 100 eq./Ru) were loaded altogether in a 60 ml autoclave equipped with a mechanical stirring device. Sealed autoclave was then purged under stirring with nitrogen (3 times 5 bars) and hydrogen (3 times 5 bars) before being pressurized to 30 bars hydrogen. It was then heated to 90° C. and hydrogen pressure was maintained to 30 bars for several hours. Upon reaction completion or after 24 h, autoclave was then cooled down to 25° C. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and yield was calculated based on GC purity of distilled product.

| | Time[1] | Conv.[2] | Yield[3] | Remarks |
|---|---|---|---|---|
| Complex according the invention | | | | |
| (dppae)(dppe)Ru(OCOC$_6$H$_5$)$_2$ | 6 | 100 | 99 | no tBuOK added |
| (dppae)(dppe)Ru(OCO$^t$Bu)$_2$ | 3 | 100 | 99 | no tBuOK added |
| Comparative complexes* | | | | |
| (En)(dppe)RuCl$_2$ | 24 | 0 | 0 | no tBuOK added |
| (En)(dppe)RuCl$_2$ | 24 | 100 | 10 | 100 eq. tBuOK/Ru 90 wt. % residues |
| (En)(dppe)Ru(H)Cl | 24 | 0 | 0 | no tBuOK added |
| (En)(dppe)Ru(H)Cl | 24 | 100 | 15 | 100 eq. tBuOK/Ru 85 wt. % residues |
| (En)(dppe)Ru(H)(HBH$_3$) | 24 | 17 | 17 | no tBuOK added |
| [(En)(dppe)(OAc)][BF$_4$] | 24 | 30 | 30 | no tBuOK added |
| [(En)(dppe)[BF$_4$]$_2$ | 24 | 22 | 22 | no tBuOK added |
| (En)(dppe)Ru(OAc)$_2$ | 24 | 25 | 25 | no tBuOK added |
| (En)(dppe)Ru(OCOC$_2$H$_5$)$_2$ | 24 | 26 | 26 | no tBuOK added |
| (En)(dppe)Ru(OCOCF$_3$)$_2$ | 24 | 20 | 16 | no tBuOK added |

*catalyst of the prior art and not being of formula (1)
[1]In hours
[2]Conversion of the starting aldehyde in % (GC)
[3]Isolated yield of the primary alcohol obtained (mol. %)
En: ethylenediamine (NN)
dppe: 1,2-bis(diphenylphosphino)ethane (PP)
dppae: 2-(diphenylphosphino)ethanamine (PN)

Influence of Nature of Ruthenium Precursor on Catalytic Activity in 2-methyl-4-((R)-2,2,3-trimethylcyclopent-3-en-1-yl)pent-4-enal Selective Hydrogenation General Procedure:

2-methyl-4-((R)-2,2,3-trimethylcyclopent-3-en-1-yl) pent-4-enal (as a 40/60 (2S,4R)/(2R,4R) diastereoisomers mixture) (10.3 g, 0.05 mol.), isopropanol (10.3 g, 100 wt. %), ruthenium complex (0.01 mmol., 0.02 mol. %) and, whenever required, tBuOK as additive (56 mg, 0.5 mmol., 1 mol. %, 50 eq./Ru) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several hours. Upon reaction completion (checked by GC) or after 24 h, autoclave was then cooled down to 25° C. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and yield was calculated based on GC purity of distilled product.

| | Time[1] | Conv.[2] | Yield[3] | Remarks |
|---|---|---|---|---|
| Complex according the invention | | | | |
| (dppae)(dppe)Ru(OCOC$_6$H$_5$)$_2$ | 9 | 100 | 99 | no tBuOK added |
| (dppae)(dppe)Ru(OCO$^t$Bu)$_2$ | 7 | 100 | 99 | no tBuOK added |
| Comparative complexes* | | | | |
| (En)(dppe)RuCl$_2$ | 24 | 0 | 0 | no tBuOK added |
| (En)(dppe)RuCl$_2$ | 24 | 100 | 12 | 100 eq. tBuOK/Ru 95 wt. % residues |
| (En)(dppe)Ru(H)Cl | 24 | 0 | 0 | no tBuOK added |
| (En)(dppe)Ru(H)Cl | 24 | 100 | 20 | 100 eq. tBuOK/Ru 80 wt. % residues |
| (En)(dppe)Ru(H)(HBH$_3$) | 24 | 15 | 15 | no tBuOK added |
| (En)(dppe)Ru(H)(HBH$_3$) | 24 | 100 | 18 | 100 eq. tBuOK/Ru 82 wt. % residues |
| [(En)(dppe)Ru(OAc)][BF$_4$] | 24 | 14 | 14 | no tBuOK added |
| [(En)(dppe)Ru][BF$_4$]$_2$ | 24 | 22 | 22 | no tBuOK added |
| (En)(dppe)Ru(OAc)$_2$ | 24 | 25 | 25 | no tBuOK added |
| (En)(dppe)Ru(OCOC$_2$H$_5$)$_2$ | 24 | 23 | 23 | no tBuOK added |
| (En)(dppe)Ru(OCOCF$_3$)$_2$ | 24 | 20 | 15 | no tBuOK added |

*catalyst of the prior art and not being of formula (1)
[1] In hours
[2] Conversion of the starting aldehyde in % (GC)
[3] Isolated yield of the primary alcohol obtained (mol. %)
En: ethylenediamine (NN)
dppe: 1,2-bis(diphenylphosphino)ethane (PP)
dppae: 2-(diphenylphosphino)ethanamine (PN)

Example 3

Catalytic Hydrogenation of Aldehydes Using the Invention's Process: Influence of the R Group on the Reactivity of the Catalysts Influence of Nature of Carboxylate Ligand on Catalytic Activity in 2-methyl-4-((R)-2,2,3-trimethylcyclopent-3-en-1-yl)pent-4-enal Selective Hydrogenation General Procedure:
2-methyl-4-((R)-2,2,3-trimethylcyclopent-3-en-1-yl)pent-4-enal (as a 40/60 (2S,4R)/(2R,4R) diastereoisomers mixture) (20.6 g, 0.1 mol) and [2-(diphenyl phosphino)ethanamine][1,2bis(diphenylphosphino)ethane]ruthenium(biscarboxylate) complex (0.01 mmol., 0.01 mol. %) were loaded altogether in a 60 ml autoclave equipped with a mechanical stirring device. Sealed autoclave was then purged under stirring with nitrogen (3 times 5 bars) and hydrogen (3 times 5 bars) before being pressurized to 50 bars hydrogen. It was then heated to 100° C. and hydrogen pressure was maintained to 50 bars for several hours. Upon reaction completion or after 48 h, autoclave was then cooled down to 25° C. and product purity was checked by GC analysis. It was then depressurized and purged with nitrogen (3 times 5 bars). Crude neat product was then flash distilled in order to determine the quantity of residues formed during the reaction and isolated yield was calculated based on GC purity of distilled product.

| | Time[1] | Conv.[2] | Yield[3] | Remarks |
|---|---|---|---|---|
| Complex according the invention (R group) | | | | |
| $^i$PrCH$_2$ | 48 | 75 | 75 | conv. 4 h: 50% GC |
| cyclopropyl | 24 | 100 | 99 | conv. 4 h: 65% GC |
| cyclohexyl | 17 | 100 | 99 | conv. 4 h: 79% GC |
| $^i$Pr | 14 | 100 | 99 | conv. 4 h: 85% GC |
| Ph | 14 | 100 | 99 | conv. 4 h: 85% GC |
| 1-adamantyl | 10 | 100 | 99 | conv. 4 h: 90% GC |
| $^t$Bu | 6 | 100 | 99 | conv. 4 h: 94% GC |
| $^t$BuCH$_2$ | 6 | 100 | 99 | conv. 4 h: 94% GC |
| (Et)(Me)$_2$C | 4 | 100 | 99 | |
| Comparative complexes* (R group) | | | | |
| *CF$_3$ | 48 | 15 | 10 | |
| *Me | 48 | 15 | 15 | |
| *Et | 48 | 18 | 18 | |

*catalyst not being of formula (1)
[1] In hours
[2] Conversion of the starting aldehyde in % (GC)
[3] Isolated yield of the primary alcohol obtained (mol. %)
En: ethylenediamine (NN)
dppe: 1,2-bis(diphenylphosphino)ethane (PP)
dppae: 2-(diphenylphosphino)ethanamine (PN)

Example 4

Catalytic Hydrogenation of Aldehydes Using the Invention Process: Influence of the PP or PN Ligands on the Reactivity of the Catalysts Influence of Nature of Diphosphine Ligand General Procedure:
3,6,7-Trimethyl-octa-2,6-dienal (as a 40/60 Z/E isomers mixture) (12.62 g, 0.075 mol), octane (12.62 g, 100 wt. %) and (2-(diphenylphosphino)ethanamine) (diphosphine)ruthenium(bispivalate) complex (0.00375 mmol., 0.005 mol. %) were loaded altogether in a 60 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars for several hours. Upon reaction completion or after 48 h, autoclave was then cooled down to 25° C. and product purity was checked by GC analysis. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and isolated yield was calculated according to GC purity of distilled product.

| Diphosphine ligand PP | Time[1] | Conv.[2] | Yield[3] | Remarks |
|---|---|---|---|---|
| bis(diphenylphosphino)methane (dppm) | 17 | 100 | 99 | conv. 4 h: 77% GC |

-continued

| Diphosphine ligand PP | Time[1] | Conv.[2] | Yield[3] | Remarks |
|---|---|---|---|---|
| 1,2-bis(diphenylphosphino)ethane (dppe) | 8.5 | 100 | 99 | conv. 4 h >90% GC |
| 1,3-bis(diphenylphosphino)propane (dppp) | 8.5 | 100 | 99 | conv. 4 h >90% GC |
| 1,4-bis(diphenylphosphino)butane (dppb) | 8 | 100 | 99 | conv. 4 h >90% GC |
| (oxybis(2,1-phenylene))bis(diphenylphosphine) (dpephos) | 7 | 100 | 99 | conv. 4 h >90% GC |
| 2,2'-bis(diphenylphosphino)-1,1'-binaphthalene (rac-Binap) | 6 | 100 | 99 | conv. 4 h >90% GC |
| 1,1'-bis(diphenylphosphino)ferrocene (dppFc) | 6 | 100 | 99 | conv. 4 h >90% GC |
| 9,9-dimethyl-4,5-bis(diphenylphosphino)xanthene (Xantphos) | 4 | 100 | 99 | |

[1]In hours
[2]Conversion of the starting aldehyde in % (GC)
[3]Isolated yield of the primary alcohol obtained (mol. %)

Influence of Nature of Aminophosphine Ligand

General Procedure:
3,6,7-Trimethyl-octa-2,6-dienal (as a 40/60 Z/E isomers mixture) (12.62 g, 0.075 mol), octane (12.62 g, 100 wt. %) and (aminophosphine)(9,9-dimethyl-4,5-bis(diphenylphosphino)xanthene)ruthenium(bispivalate) complex (0.00375 mmol, 0.005 mol. %) were loaded altogether in a 60 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars for several hours. Upon reaction completion or after 48 h, autoclave was then cooled down to 25° C. and product purity was checked by GC analysis. It was then depressurized and purged with nitrogen (3 times 5 bars) and reaction mixture was then transferred to a round-bottomed flask and solvent was removed under vacuum. Crude product was then flash distilled in order to determine the quantity of residues formed during the reaction and isolated yield was calculated according to GC purity of distilled product.

| Aminophosphine ligand PN | Time[1] | Conv.[2] | Yield[3] | Remarks |
|---|---|---|---|---|
| 2-(di-isopropylphosphino)ethanamine | 8 | 100 | 99 | conv. 4 h >90% GC |
| 2-(di-tert-butylphosphino)ethanamine | 6 | 100 | 99 | conv. 4 h >90% GC |
| 2-(diphenylphosphino)phenyl)methanamine | 5 | 100 | 99 | conv. 4 h >90% GC |
| 3-(diphenylphosphino)propan-1-amine | 4.5 | 100 | 99 | conv. 4 h >90% GC |
| 2-(diphenylphosphino)ethanamine (dppae) | 4 | 100 | 99 | |

[1]In hours
[2]Conversion of the starting aldehyde in % (GC)
[3]Isolated yield of the primary alcohol obtained (mol. %)

Example 5

Catalytic Hydrogenation of Aldehydes Using the Invention Process: Influence of the Additive and In Situ Generation of the Complex (1)

Influence of Acidic Additive and In Situ Generation of Complex (1)

General Procedure:
2-methyl-4-((R)-2,2,3-trimethylcyclopent-3-en-1-yl)pent-4-enal (as a 40/60 (2S,4R)/(2R,4R) diastereoisomers mixture) (20.66 g, 0.1 mol), ruthenium complex (0.01 mmol., 0.01 mol. %) and, whenever required, pivalic acid as additive (102 mg, 1 mmol, 1 mol. %) were loaded altogether in a 60 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars for several hours. Upon reaction completion or after 48 h, autoclave was then cooled down to 25° C. and product purity was checked by GC analysis. It was then depressurized and purged with nitrogen (3 times 5 bars). Crude neat product was then flash distilled in order to determine the quantity of residues formed during the reaction and isolated yield was calculated based on GC purity of distilled product.

| Ruthenium catalyst | Pivalic acid | Time[1] | Conv.[2] | Yield[3] |
|---|---|---|---|---|
| (dppae)(dppe)Ru(OCO$^t$Bu)$_2$ | no | 6 | 100 | 99 |
| (dppae)(dppe)Ru(OCO$^t$Bu)$_2$ | yes | 2 | 100 | 99 |

[1]In hours
[2]Conversion of the starting aldehyde in % (GC)
[3]Isolated yield of the primary alcohol obtained (mol. %)
dppae: 2-(diphenylphosphino)ethanamine (PN)
dppe: 1,2-bis(diphenylphosphino)ethane (PP)

Influence of Acidic Additives on Catalytic Activity

General Procedure:
3,7-dimethyloct-6-enal (30.85 g, 0.2 mol), [2-(diphenylphosphino) ethanamine][1,2-bis(diphenylphosphino)ethane] ruthenium(bispivalate) complex (4.6 mg, 0.005 mmol., 0.0025 mol. %) and acidic additive (2 mmol., 1 mol. %) were loaded altogether in a 60 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was then increased and maintained to 50 bars for several hours. Upon reaction completion or after 72 h, autoclave was then cooled down to 25° C. It was then depressurized and purged with nitrogen (3 times 5 bars). Crude neat product was then flash distilled in order to determine the quantity of residues formed during the reaction and yield was calculated based on GC purity of distilled product.

| Acidic additive | Time[1] | Conv.[2] | Yield[3] | Remarks |
|---|---|---|---|---|
| none | 48 | 80 | 79 | blocked after 24 h |
| Hexylboronic acid | 48 | 100 | 98 | |
| Diphenylphosphinic acid | 44 | 100 | 98 | |
| 2,4-dichlorobenzoic acid | 40 | 100 | 98 | |
| 2,4,6-trimethylbenzoic acid | 24 | 100 | 99 | |
| pentafluorophenol | 24 | 100 | 99 | |
| 4-methoxyphenol | 24 | 100 | 99 | |
| 4-nitrobenzoic acid | 20 | 100 | 99 | |
| 4-carbomethoxyphenol | 16 | 100 | 99 | |
| (1R)-1,2,2-trimethylcyclopentane-1,3-dicarboxylic acid (camphoric acid) | 15 | 100 | 99 | |
| Terephtalic acid | 14 | 100 | 99 | |
| 4-methoxybenzoic acid | 12 | 100 | 99 | |
| 3,4,5-trimethoxybenzoic acid | 12 | 100 | 99 | |
| 1-naphtoic acid | 12 | 100 | 99 | |
| 4-(tert-butyl)benzoic acid | 12 | 100 | 99 | |
| 4-biphenylcarboxylic acid | 12 | 100 | 99 | |
| Benzoic acid | 12 | 100 | 99 | |
| 4-nitrophenol | 12 | 100 | 99 | |
| 2-naphtoic acid | 10 | 100 | 99 | |
| 1-adamantane carboxylic acid | 10 | 100 | 99 | |
| Pivalic acid | 9 | 100 | 99 | |
| 3,3-dimethylbutanoic acid | 9 | 100 | 99 | |
| 2,2-dimethylbutanoic acid | 8 | 100 | 99 | |

[1]In hours
[2]Conversion of the starting aldehyde in % (GC)
[3]Isolated yield of the primary alcohol obtained (mol. %)
dppae: 2-(diphenylphosphino)ethanamine; dppe: 1,2-bis(diphenylphosphino)ethane.

Despite that the amount of the catalyst in this example is half of the above examples, the additive allows to reach similar conversions and reaction time.

Example 6

Catalytic Hydrogenation of Various Aldehydes Using the Invention Process 3,6,7-Trimethyl-octa-2,6-dien-1-ol synthesis 3,6,7-Trimethyl-octa-2,6-dienal (as a 40/60 Z/E isomers mixture) (166 g, 1 mol.), heptanes (332 g, 200 wt. %, technical grade), pivalic acid (0.510 g, 5 mmol., 0.5 mol. %) and [2-(diphenylphosphino)ethanamine][9,9-dimethyl-4,5-bis(diphenylphosphino)xanthene]ruthenium(bispivalate) complex (56 mg, 0.05 mmol., 0.005 mol. %) were loaded altogether in a 1 L autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 80° C. and hydrogen pressure was then increased and maintained to 50 bars during all the reaction to afford desired product with 96% selectivity as a 40/60 Z/E isomers mixture. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation followed by further fractional distillation, pure 3,6,7-trimethyloct-2,6-dien-1-ol was obtained in 91% yield.

3,6,7-trimethyloct-6-en-1-ol synthesis 3,6,7-Trimethyloct-6-enal (168 g, 1 mol.), 2,2-dimethylbutanoic acid (0.581 g, 5 mmol., 0.5 mol. %) and [2-(diphenylphosphino)ethanamine][1,2-bis(diphenylphosphino)ethane]ruthenium(bispivalate) complex (23 mg, 0.025 mmol, 0.0025 mol. %) were loaded altogether in a 300 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with complete selectivity. Upon reaction completion (checked by both hydrogen consumption and GC), autoclave was cooled down to 25° C. It was then depressurized and purged with nitrogen (3 times 5 bars). After flash distillation, pure 3,6,7-trimethyloct-6-en-1-ol was obtained in 99% yield.

3,7-dimethylocta-2,6-dien-1-ol synthesis 3,7-Trimethyl-octa-2,6-dienal (as a 40/60 Z/E isomers mixture) (152 g, 1 mol.), heptane (304 g, 200 wt. %, technical grade), benzoic acid (0.610 g, 5 mmol, 0.5 mol. %) and [2-(diphenylphosphino)ethanamine][9,9-dimethyl-4,5-bis(diphenylphosphino)xanthene]ruthenium(bisbenzoate) complex (58 mg, 0.05 mmol., 0.005 mol. %) were loaded altogether in a 1 L autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 80° C. and hydrogen pressure was then increased and maintained to 50 bars during all the reaction to afford desired product with 95% selectivity. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation followed by further fractional distillation, pure 3,7-dimethyloct-2,6-dien-1-ol was obtained in 90% yield.

3,7-dimethyloct-6-en-1-ol synthesis 3,7-Dimethyloct-6-enal (154 g, 1 mol.), 3,3-dimethylbutanoic acid (0.581 g, 5 mmol, 0.5 mol. %) and [2-(diphenylphosphino)ethanamine][1,2-bis(diphenylphosphino)ethane]ruthenium(biscyclopropanecarboxylate) complex (22 mg, 0.025 mmol., 0.0025 mol. %) were loaded altogether in a 300 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with complete selectivity. Upon reaction completion (checked by both hydrogen consumption and GC), autoclave was cooled down to 25° C. It was then depressurized and purged with nitrogen (3 times 5 bars). After flash distillation, pure 3,7-trimethyloct-6-en-1-ol was obtained in 99% yield.

3-methylhex-2-en-1-ol synthesis

3-Methylhex-2-enal (as a 40/60 Z/E isomers mixture) (112 g, 1 mol.), heptane (224 g, 200 wt. %, technical grade), benzoic acid (0.610 g, 5 mmol., 0.5 mol. %) and [2-(diphenylphosphino)ethanamine][9,9-dimethyl-4,5-bis(diphenylphosphino)xanthene]ruthenium(bispivalate) complex (56 mg, 0.05 mmol., 0.005 mol. %) were loaded altogether in a 1 L autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 80° C. and hydrogen pressure was then increased and maintained to 50 bars during all the reaction to afford desired product with 96% selectivity as a 40/60 Z/E isomers mixture. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation followed by further fractional distillation, pure 3-methylhex-2-en-1-ol was obtained in 91% yield.

3-methylhex-2-en-1-yl acetate synthesis

Aldehyde base-free chemoselective hydrogenation reaction can also efficiently be run in the presence of 1 molar equivalent of acetic anhydride in order to directly afford the acetate (via reduction of the aldehyde into the alcohol which reacts with the anhydride to provide the ester).

3-Methylhex-2-enal (as a 40/60 Z/E isomers mixture) (112 g, 1 mol.), acetic anhydride (107 g, 1.05 mol) and [2-(diphenylphosphino)ethanamine][1,2-bis(diphenylphosphino) ethane]ruthenium(bispivalate) complex (93 mg, 0.1 mmol., 0.01 mol. %) were loaded altogether in a 1 L autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with 98% selectivity as a 40/60 WE isomers mixture. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and concentrated under vacuum. After initial flash distillation followed by further fractional distillation, pure 3-methylhex-2-en-1-yl acetate was obtained in 94% yield.

(E)-2-methylpent-2-en-1-ol synthesis (E)-2-Methylpent-2-enal (98 g, 1 mol.), heptane (196 g, 200 wt. %, technical grade), benzoic acid (0.610 g, 5 mmol., 0.5 mol. %) and [2-(diphenylphosphino)ethanamine][9,9-dimethyl-4,5-bis(diphenylphosphino)xanthene]ruthenium (bispivalate) complex (56 mg, 0.05 mmol., 0.005 mol. %) were loaded altogether in a 1l autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 80° C. and hydrogen pressure was then increased and maintained to 50 bars during all the reaction to afford desired product with 98% selectivity. Upon reaction completion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation followed by further fractional distillation, pure (E)-2-methylpent-2-en-1-ol was obtained in 93% yield.

(E)-4-methyl-5-(p-tolyl)pent-4-enal synthesis (E)-4-Methyl-5-(p-tolyl)pent-4-enal (47 g, 0.25 mol.), pivalic acid (0.13 g, 1.25 mmol., 0.5 mol. %) and [2-(diphenylphosphino)ethanamine][1,2-bis(diphenylphosphino)ethane]ruthenium(bis-isobutyrate) complex (5.7 mg, 0.00625 mmol., 0.0025 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with complete selectivity. After complete reaction conversion (checked by both hydrogen consumption and GC), autoclave was cooled down to 25° C. It was then depressurized and purged with nitrogen (3 times 5 bars). After flash distillation, pure (E)-4-methyl-5-(p-tolyl)pent-4-en-1-ol was obtained in 99% yield.

2,3-dimethylbut-2-en-1-ol synthesis 2,3-Dimethylbut-2-enal (490 g, 5 mol.), 2,2-dimethylbutanoic acid (2.9 g, 0.025 mol., 0.5 mol. %) and [2-(diphenylphosphino)ethanamine][9,9-dimethyl-4,5-bis(diphenylphosphino)xanthene]ruthenium(bispivalate) complex (185 mg, 0.166 mmol., 0.0033 mol. %) were loaded altogether in a 1 L autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with complete selectivity. After complete reaction conversion (checked by both hydrogen consumption and GC), autoclave was cooled down to 25° C. It was then depressurized and purged with nitrogen (3 times 5 bars). After flash distillation, pure 2,3-dimethylbut-2-en-1-ol was obtained in 99% yield.

(Z)-oct-5-en-1-ol synthesis (Z)-Oct-5-enal (63 g, 0.5 mol.), heptane (126 g, 200 wt. %, technical grade), pivalic acid (0.13 g, 1.25 mmol, 0.25 mol. %) and [2-(diphenylphosphino)ethanamine][9,9-dimethyl-4,5-bis(diphenylphosphino)xanthene]ruthenium (bispivalate) complex (83 mg, 0.075 mmol., 0.015 mol. %) were loaded altogether in a 1 L autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 70° C. and hydrogen pressure was then increased and maintained to 50 bars during all the reaction to afford desired product with 97% selectivity. After complete reaction conversion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation and further fractional distillation, highly pure (Z)-oct-5-en-1-ol was obtained in 92% yield.

Undec-10-en-1-ol synthesis

Undec-10-enal (84 g, 0.5 mol.), heptane (168 g, 100 wt. %, technical grade), pivalic acid (0.13 g, 1.25 mmol, 0.25 mol. %) and [2-(diphenylphosphino)ethanamine][9,9-dimethyl-4,5-bis(diphenylphosphino)xanthene]ruthenium (bispivalate) complex (83 mg, 0.075 mmol., 0.015 mol. %) were loaded altogether in a 1 L autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 70° C. and hydrogen pressure was then increased and maintained to 50 bars during all the reaction to afford desired product with 94% selectivity. After complete reaction conversion (checked by both hydrogen consumption and GC), autoclave was cooled down to 25° C. It was then depressurized and purged with nitrogen (3 times 5 bars) and reaction mixture was then transferred to a round-bottomed flask and solvent was removed under vacuum. After initial flash distillation and further fractional distillation, highly pure undec-10-en-1-ol was obtained in 90% yield.

(2,6,6-trimethylcyclohex-2-en-1-yl)methanol synthesis (2,6,6-trimethylcyclohex-2-ene)carbaldehyde (76 g, 0.5 mol.), benzoic acid (0.31 g, 2.5 mmol, 0.5 mol. %) and [2-(diphenylphosphino)ethanamine][1,4-bis(diphenylphosphino)butane]ruthenium(bispivalate) complex (12.0 mg, 0.0125 mmol., 0.0025 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with complete selectivity. After complete reaction conversion (checked by both hydrogen consumption and GC), autoclave was cooled down to 25° C. It was then depressurized and purged with nitrogen (3 times 5 bars). After flash distillation, pure (2,6,6-trimethylcyclohex-2-en-1-yl)methanol was obtained in 99% yield.

(2,6,6-trimethylcyclohex-1-en-1-yl)methanol synthesis (2,6,6-trimethylcyclohex-1-ene)carbaldehyde (76 g, 0.5 mol.), benzoic acid (0.31 g, 2.5 mmol, 0.5 mol. %) and [2-(diphenylphosphino)ethanamine][1,4-bis(diphenylphosphino)propane]ruthenium(bispivalate) complex (24.0 mg, 0.025 mmol., 0.005 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with complete selectivity. After complete reaction conversion (checked by both hydrogen consumption and GC), autoclave was cooled down to 25° C. It was then depressurized and purged with nitrogen (3 times 5 bars). After flash distillation, pure (2,6,6-trimethylcyclohex-1-en-1-yl)methanol was obtained in 99% yield.

Trans-(2,5,6,6-tetramethylcyclohex-2-en-1-yl)methanol synthesis

Racemic trans-(2,5,6,6-tetramethylcyclohex-2-ene)carbaldehyde (83 g, 0.5 mol.), benzoic acid (0.31 g, 2.5 mmol, 0.5 mol. %) and [2-(diphenylphosphino)ethanamine][1,2-bis(diphenylphosphino)ethane]ruthenium(bispivalate) complex (11.7 mg, 0.0125 mmol., 0.0025 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with complete selectivity. After complete reaction conversion (checked by both hydrogen consumption and GC), autoclave was cooled down to 25° C. It was then depressurized and purged with nitrogen (3 times 5 bars). After flash distillation, pure racemic trans-(2,5,6,6-tetramethylcyclohex-2-en-1-yl)methanol was obtained in 99% yield.

(2,5,6,6-tetramethylcyclohex-1-en-1-yl)methanol synthesis (2,5,6,6-tetramethylcyclohex-1-ene)carbaldehyde (41.5 g, 0.25 mol.), pivalic acid (0.13 g, 1.25 mmol, 0.5 mol. %) and [2-(diphenylphosphino)ethanamine][1,4-bis(diphenylphosphino)ethane]ruthenium(bis-cyclohexanecarboxylate) complex (12.3 mg, 0.0125 mmol., 0.005 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with complete selectivity. After complete reaction conversion (checked by both hydrogen consumption and GC), autoclave was cooled down to 25° C. It was then depressurized and purged with nitrogen (3 times 5 bars). After flash distillation, pure (2,5,6,6-tetramethylcyclohex-1-en-1-yl)methanol was obtained in 99% yield.

(R)-2-ethyl-4-(2,2,3-trimethylcyclopent-3-en-1-yl)but-2-en-1-ol synthesis (R)-2-ethyl-4-(2,2,3-trimethylcyclopent-3-en-1-yl)but-2-enal (as a 95/5 E/Z isomers mixture) (206 g, 1 mol.), benzoic acid (0.61 g, 5 mmol., 0.5 mol. %) and [2-(diphenylphosphino)ethanamine][9,9-dimethyl-4,5-bis(diphenylphosphino)xanthene]ruthenium(bispivalate) complex (55.1 mg, 0.05 mmol., 0.005 mol. %) were loaded altogether in a 1 L autoclave equipped with a mechanical stirring device. Sealed autoclave was then purged under stiffing with nitrogen (3 times 5 bars) and hydrogen (3 times 5 bars) before being pressurized to 10 bars hydrogen. It was then heated to 100° C. and hydrogen pressure was then increased and maintained to 15 bars during all the reaction to afford desired product with 99.5% selectivity as a 95/5 E/Z isomers mixture and no loss of optical purity. Upon complete reaction conversion (checked by both hydrogen consumption and GC), autoclave was cooled down to 25° C. It was then depressurized and purged with nitrogen (3 times 5 bars). After flash distillation, highly pure (R)-2-ethyl-4-(2,2,3-trimethylcyclopent-3-en-1-yl)but-2-en-1-ol was obtained in 98.5% yield.

(R)-2-methyl-4-(2,2,3-trimethylcyclopent-3-en-1-yl)but-2-en-1-ol synthesis (R)-2-methyl-4-(2,2,3-trimethylcyclopent-3-en-1-yl)but-2-enal (as a 98/2 E/Z isomers mixture) (48.1 g, 0.25 mol.), 1-naphtoic acid (0.215 g, 1.25 mmol., 0.5 mol. %) and [2-(diphenylphosphino)ethanamine][9,9-dimethyl-4,5-bis(diphenylphosphino)xanthene]ruthenium(bispivalate) complex (13.9 mg, 0.0125 mmol., 0.005 mol. %) were loaded altogether in a 120 ml autoclave equipped with a mechanical stiffing device. Sealed autoclave was then purged under stiffing with nitrogen (3 times 5 bars) and hydrogen (3 times 5 bars) before being pressurized to 5 bars hydrogen. It was then heated to 100° C. and hydrogen pressure was then increased and maintained to 10 bars during all the reaction to afford desired product with 98.5% selectivity as a 98/2 E/Z isomers mixture and no loss of optical purity. Upon complete reaction conversion (checked by both hydrogen consumption and GC), autoclave was cooled down to 25° C. It was then depressurized and purged with nitrogen (3 times 5 bars). After flash distillation, highly pure (R)-2-methyl-4-(2,2,3-trimethylcyclopent-3-en-1-yl)but-2-en-1-ol was obtained in 97.5% yield.

2-methyl-4-((S)-2,2,3-trimethylcyclopent-3-en-1-yl)butan-1-ol synthesis 2-methyl-4-((S)-2,2,3-trimethylcyclopent-3-en-1-yl)butanal (as a 50/50 diastereoisomers mixture) (48.5 g, 0.25 mol.), benzoic acid (0.152 g, 1.25 mmol., 0.5 mol. %) and [2-(diphenylphosphino)ethanamine][1,2-bis(diphenylphosphino)ethane]ruthenium (bispivalate) complex (5.8 mg, 0.00625 mmol., 0.0025 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 5 bars hydrogen. It was then heated to 100° C. and hydrogen pressure was then increased and maintained to 10 bars during all the reaction to afford desired product with complete selectivity as a 50/50 diastereoisomers mixture and no loss of optical purity. Upon complete reaction conversion (checked by both hydrogen consumption and GC), autoclave was cooled down to 25° C. It was then depressurized and purged with nitrogen (3 times 5 bars). After flash distillation, highly pure 2-methyl-4-((S)-2,2,3-trimethylcyclopent-3-en-1-yl)butan-1-ol was obtained in more than 99% yield.

hexa-2,4-dien-1-yl pivalate synthesis

In the case of hexa-2,4-dienal, if aldehyde base-free chemoselective hydrogenation reaction generally afforded desired product in much better yields compared to classical systems due to really high starting material sensitivity to basic conditions, catalytic activity was then noticeably increased running the reaction in the presence of 1 molar equivalent of various carboxylic acid anhydrides in order to afford hexa-2,4-dien-1-ol esters via reduction of the aldehyde into the alcohol which reacts with anhydride used to provide the corresponding ester.

Hexa-2,4-dienal (as a 85/15 (E,E)/(Z,E) isomers mixture) (24 g, 0.25 mol.), pivalic anhydride (48.8 g, 0.26 mol.) and [2-(diphenylphosphino)ethanamine][9,9-dimethyl-4,5-bis(diphenylphosphino)xanthene]ruthenium(bispivalate) complex (27.8 mg, 0.025 mmol., 0.01 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was then increased and maintained to 50 bars during all the reaction to afford desired product with 98% selectivity as a 85/15 (E,E)/(Z,E) isomers mixture. Upon reaction completion (checked by both hydrogen consumption and GC), autoclave was then cooled down to 25° C. It was then depressurized and purged with nitrogen (3 times 5 bars). After flash distillation, highly pure hexa-2,4-dien-1-yl pivalate was obtained in 96% yield.

3-((R)-4-methylcyclohex-3-en-1-yl)butan-1-ol synthesis 3-((R)-4-methylcyclohex-3-en-1-yl)butanal (as a 50/50 diastereoisomers mixture) (41.6 g, 0.25 mol.), benzoic acid (0.152 g, 1.25 mmol., 0.5 mol. %) and [3-(diphenylphosphino)propan-1-amine][1,2-bis(diphenylphosphino)ethane]ruthenium(bispivalate) complex (5.9 mg, 0.00625 mmol., 0.0025 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 5 bars hydrogen. It was then heated to 100° C. and hydrogen pressure was then increased and maintained to 10 bars during all the reaction to afford desired product with complete selectivity as a 50/50 diastereoisomers mixture and no loss of optical purity. Upon complete reaction conversion (checked by both hydrogen consumption and GC), autoclave was cooled down to 25° C. It was then depressurized and purged with nitrogen (3 times 5 bars). After flash distillation, highly pure 3-((R)-4-methylcyclohex-3-en-1-yl)butan-1-ol was obtained in more than 99.0% yield.

Example 7

Catalytic Hydrogenation of Various Aldehydes Using the Invention's Process: Chemoselectivity 1-((1S,3R)-3-(2-hydroxyethyl)-2,2-dimethylcyclopropyl)propan-2-one synthesis 2-((1R,3S)-2,2-Dimethyl-3-(2-oxopropyl)cyclopropyl)acetaldehyde (16.8 g, 0.1 mol.), toluene (50.4 g, 300 wt. %) and [2-(diphenylphosphino)ethanamine][9,9-dimethyl-4,5-bis(diphenylphosphino)xanthene]ruthenium(bispivalate) complex (16.7 mg, 0.015 mmol, 0.015 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was then increased and maintained to 50 bars during all the reaction to afford desired product with 97% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum.

After flash chromatography, highly pure 1-((1S,3R)-3-(2-hydroxyethyl)-2,2-dimethylcyclopropyl)propan-2-one was obtained in 94% yield.

1-((1S,3S)-3-(2-hydroxyethyl)-2,2-dimethylcyclobutyl)ethanone synthesis 2-((1S,3S)-3-Acetyl-2,2-dimethylcyclobutyl)acetaldehyde (16.8 g, 0.1 mol.), toluene (50.4 g, 300 wt. %) and [(2-(diphenylphosphino)ethanamine)[1,1'-bis(diphenylphosphino)ferrocene]ruthenium(bispivalate) complex (16.3 mg, 0.015 mmol, 0.015 mol. %) were loaded altogether in a 125 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was then increased and maintained to 50 bars during all the reaction to afford desired product with complete selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash distillation, highly pure 1-((1S,3S)-3-(2-hydroxyethyl)-2,2-dimethylcyclobutyl) ethanone was obtained in more than 99% yield.

4-((1R,2S)-2-(hydroxymethyl)-3,3-dimethyl-7-methylenecycloheptyl)butan-2-one synthesis (1S,7R)-2,2-Dimethyl-6-methylene-7-(3-oxobutyl)cycloheptanecarbaldehyde (11.8 g, 0.05 mol.), heptane (70.8 g, 600 wt. %, technical grade) and [2-(diphenylphosphino)ethanamine][9,9-dimethyl-4,5-bis(diphenylphosphino)xanthene]ruthenium(bispivalate) complex (11.1 mg, 0.01 mmol, 0.02 mol. %) were loaded altogether in a 200 ml autoclave equipped with a mechanical stirring device. Sealed autoclave was then purged under stirring with nitrogen (3 times 5 bars) and hydrogen (3 times 5 bars) before being pressurized to 10 bars hydrogen. It was then heated to 80° C. and hydrogen pressure was then increased and maintained to 30 bars during all the reaction to afford desired product with 96% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, 4-((1R,2S)-2-(hydroxymethyl)-3,3-dimethyl-7-methylenecycloheptyl) highly pure butan-2-one was obtained in 92% yield.

4-((1R,4S)-4-(5-hydroxypent-1-en-2-yl)-2,2-dimethylcyclobutyl)butan-2-one synthesis 4-((1S,2R)-3,3-Dimethyl-2-(3-oxobutyl)cyclobutyl)pent-4-enal (11.8 g, 0.05 mol.), methyl(tert-butyl)ether (70.8 g, 600 wt. %) and [2-(diphenylphosphino)ethanamine][9,9-dimethyl-4,5-bis(diphenylphosphino)xanthene]ruthenium (bispivalate) complex (11.1 mg, 0.01 mmol, 0.02 mol. %) were loaded altogether in a 200 ml autoclave equipped with a mechanical stirring device. Sealed autoclave was then purged under stirring with nitrogen (3 times 5 bars) and hydrogen (3 times 5 bars) before being pressurized to 10 bars hydrogen. It was then heated to 80° C. and hydrogen pressure was then increased and maintained to 30 bars during all the reaction to afford desired product with 98% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, highly pure 4-((1R,4S)-4-(5-hydroxypent-1-en-2-yl)-2,2-dimethylcyclobutyl)butan-2-one was obtained in 95% yield.

Racemic endo 1-(3-(2-hydroxyethyl)bicyclo[2.2.1]heptan-2-yl)propan-2-one synthesis Racemic endo 2-(3-(2-oxopropyl)bicyclo[2.2.1]heptan-2-yl)acetaldehyde (19.4 g, 0.1 mol.), toluene (58.2 g, 300 wt. %) and [(2-(diphenylphosphino)ethanamine)[(oxybis(2,1-phenylene))bis(diphenylphosphine)]ruthenium(bispivalate) complex (10.7 mg, 0.01 mmol, 0.01 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was then increased and maintained to 50 bars during all the reaction to afford desired product with complete selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash distillation, highly pure racemic endo 1-(3-(2-hydroxyethyl) bicyclo[2.2.1]heptan-2-yl)propan-2-one was obtained in 99% yield.

7-hydroxyheptan-2-one synthesis

6-Oxoheptanal (12.8 g, 0.1 mol.), toluene (76.8 g, 600 wt. %) and [2-(diphenylphosphino)ethanamine][9,9-dimethyl-4,5-bis(diphenylphosphino)xanthene]ruthenium(bispivalate) complex (22.2 mg, 0.02 mmol, 0.02 mol. %) were loaded altogether in a 200 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 80° C. and hydrogen pressure was maintained to 50 bars during all the reaction to afford desired product with 94% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, highly pure 7-hydroxyheptan-2-one was obtained in 90% yield.

1-(5,5-dimethylcyclohex-1-en-1-yl)-6-hydroxyhexan-1-one synthesis 6-(5,5-dimethylcyclohex-1-en-1-yl)-6-oxohexanal (11.1 g, 0.05 mol.), toluene (33.3 g, 300 wt. %) and [(2-(diphenylphosphino)ethanamine([2,2'-bis(diphenylphosphino)-1,1'-binaphthalene]ruthenium(bispivalate) complex (5.8 mg, 0.005 mmol, 0.01 mol. %) were loaded altogether in a 120 ml autoclave equipped with a mechanical stirring device. Sealed autoclave was then purged under stiffing with nitrogen (3 times 5 bars) and hydrogen (3 times 5 bars) before being pressurized to 20 bars hydrogen. It was then heated to 90° C. and hydrogen pressure was then increased and maintained to 50 bars during all the reaction to afford desired product with more than 99% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, highly pure 1-(5,5-dimethylcyclohex-1-en-1-yl)-6-hydroxyhexan-1-one was obtained in 98% yield.

1-(5,5-dimethylcyclohex-1-en-1-yl)-5-hydroxy-4-methylpentan-1-one synthesis 5-(5,5-dimethylcyclohex-1-en-1-yl)-2-methyl-5-oxopentanal (11.1 g, 0.05 mol.), toluene (33.3 g, 300 wt. %) and [2-(di-tert-butylphosphino)ethanamine][9,9-dimethyl-4,5-bis(diphenylphosphino)xanthene]ruthenium(bispivalate) complex (5.4 mg, 0.005 mmol, 0.01 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was then increased and maintained to 50 bars during all the reaction to afford desired product with 98% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash chromatography, highly pure 1-(5,5-dimethylcyclohex-1-en-1-yl)-5-hydroxy-4-methylpentan-1-one was obtained in 94% yield.

9-hydroxy-2,6-dimethylnonan-4-one synthesis 4,8-dimethyl-6-oxononanal (18.4 g, 0.1 mol.), toluene (36.8 g, 200 wt. %) and [2-(diphenylphosphino)ethanamine][9,9-dimethyl-4,5-bis(diphenylphosphino)xanthene]ruthenium(bispivalate) complex (11.1 mg, 0.01 mmol, 0.01 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was increased and maintained to 50 bars during all the reaction to afford desired product with complete selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash distillation, highly pure 9-hydroxy-2,6-dimethylnonan-4-one was obtained in 99% yield.

7-hydroxy-3-isopropyl-4-methylheptan-2-one synthesis 5-acetyl-4,6-dimethylheptanal (18.4 g, 0.1 mol., as one diastereoisomer), toluene (55.2 g, 300 wt. %) and [2-(diphenylphosphino)ethanamine][9,9-dimethyl-4,5-bis(diphenyl phosphino)xanthene]ruthenium(bispivalate) complex (22.2 mg, 0.02 mmol, 0.02 mol. %) were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 80° C. and hydrogen pressure was then increased ad maintained to 50 bars during all the reaction to afford desired product with more than 99% selectivity. Upon reaction completion (checked by both hydrogen consumption and GC), autoclave was then cooled down to 25° C. It was then depressurized and purged with nitrogen (3 times 5 bars) and reaction mixture was then transferred to a round-bottomed flask and solvent was removed under vacuum. After flash distillation, highly pure 1-(5,5-dimethylcyclohex-1-en-1-yl)-5-hydroxy-4-methylpentan-1-one was obtained in 99% yield.

Catalytic Hydrogenation of Various Aldehydes Using the Invention's Process: Chemoselectivity in Aldehyde Versus Ketone Competitive Experiments 2-methyl-4-((R)-2,2,3-trimethylcyclopent-3-en-1-yl) pent-4-enal versus (R,E)-3,3-dimethyl-5-(2,2,3-trimethylcyclopent-3-en-1-yl)pent-4-en-2-one 2-Methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), (R,E)-3,3-dimethyl-5-(2,2,3-trimethylcyclopent-3-en-1-yl)pent-4-en-2-one (11.0 g, 0.05 mol.), octane (21.3 g, 100 wt. %) and [2-(diphenylphosphino)ethanamine][1,2-bis(diphenylphosphino)ethane]ruthenium(bispivalate) complex (4.7 mg, 0.005 mmol., 0.01 mol. %/aldehyde) were loaded altogether were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 100° C. and hydrogen pressure was increased and maintained to 50 bars during all the reaction that was followed by GC analysis.

|  | t (h) | | | | | | | |
| --- | --- | --- | --- | --- | --- | --- | --- | --- |
|  | 0 | 1 | 2 | 4 | 6 | 7 | 8 | 12 |
| Aldehydic substrate (relative GC %) | 100 | 49.0 | 25.0 | 9.0 | 2.0 | 0.5 | 0 | 0 |
| Ketonic substrate (relative GC %) | 100 | 100 | 100 | 100 | 100 | 100 | 100 | 100 |
| primary vs. secondary alcohols formation selectivity (%)* |  | 100 | 100 | 100 | 100 | 100 | 100 | 100 |

*no hydrogenation of alkenes observed.
Note:
primary vs. secondary alcohol selectivity (%) = 100 × (% primary alcohol − % secondary alcohol)/(% primary alcohol + % secondary alcohol).

2-methyl-4-((R)-2,2,3-trimethylcyclopent-3-en-1-yl) pent-4-enal versus trans 1-(2,2,6-trimethylcyclohexyl)hexan-3-one 2-Methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), racemic trans 1-(2,2,6-trimethylcyclohexyl)hexan-3-one (11.2 g, 0.05 mol.), heptane (43.0 g, 200 wt. %) and [2-(diphenylphosphino)ethanamine][9,9-dimethyl-4,5-bis(diphenylphosphino)xanthene]ruthenium (bispivalate) complex (8.3 mg, 0.0075 mmol, 0.015 mol. %/aldehyde) were loaded altogether were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was increased and maintained to 50 bars during all the reaction that was followed by GC analysis.

| | t (h) | | | | | | | | |
|---|---|---|---|---|---|---|---|---|---|
| | 0 | 0.5 | 1 | 2 | 3 | 4 | 6 | 7 | 9 |
| Aldehydic substrate (relative GC %) | 100 | 66 | 48 | 31 | 16.6 | 11 | 4 | 2 | 0 |
| Ketonic substrate (relative GC %) | 100 | 100 | 99.9 | 99.8 | 99.7 | 99.6 | 99.4 | 99.3 | 99.1 |
| primary vs. secondary alcohol formation selectivity (%)* | | 99.7 | 99.6 | 99.4 | 99.3 | 99.1 | 98.8 | 98.6 | 98.2 |

*no hydrogenation of alkenes observed.
Note:
primary vs. secondary alcohol selectivity (%) = 100 × (% primary alcohol − % secondary alcohol)/(% primary alcohol + % secondary alcohol).

2-methyl-4-((R)-2,2,3-trimethylcyclopent-3-en-1-yl)pent-4-enal versus acetophenone 2-Methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), acetophenone (6.0 g, 0.05 mol.), octane (48.9 g, 300 wt. %), and [(2-(diphenylphosphino)ethanamine][1,1'-bis(diphenyl phosphino)ferrocene]ruthenium(bispivalate) complex (8.1 mg, 0.0075 mmol., 0.015 mol. %/aldehyde) were loaded altogether were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 90° C. and hydrogen pressure was increased and maintained to 50 bars during all the reaction that was followed by GC analysis.

2-methyl-4-((R)-2,2,3-trimethylcyclopent-3-en-1-yl)pent-4-enal versus 3-methylcyclopentadec-5-ynone 2-Methyl-4-((R)-2,2,3-trimethylcyclopent-3-en-1-yl)pent-4-enal (as a 40/60 (2S,4R)/(2R,4R) diastereoisomers mixture) (10.3 g, 0.05 mol), 3-methylcyclopentadec-5-ynone (11.7 g, 0.05 mol.), octane (66 g, 300 wt. %), and [(2-(diphenylphosphino)ethanamine][1,2-bis(diphenylphosphino)ethane]ruthenium(bispivalate) complex (9.3 mg, 0.01 mmol., 0.02 mol. %/aldehyde) were loaded altogether were loaded altogether in a 120 ml autoclave equipped with a mechanical stirring device. Sealed autoclave was then purged under stirring with nitrogen (3 times 5 bars) and hydrogen (3 times 5 bars) before being pressurized to 20 bars hydrogen. It was then heated to 80° C. and hydrogen pressure was increased and maintained to 50 bars during all the reaction that was followed by GC analysis.

| | t (h) | | | | | | | |
|---|---|---|---|---|---|---|---|---|
| | 0 | 0.5 | 1 | 2 | 4 | 6 | 8 | 10 |
| Aldehydic substrate (relative GC %) | 100 | 65 | 49 | 31 | 11 | 4 | 1 | 0 |
| Ketonic substrate (relative GC %) | 100 | 99.8 | 99.6 | 99.2 | 98.3 | 97.5 | 96.5 | 92.0 |
| overall selectivity (%)* | | 98.8 | 98.5 | 97.7 | 96.3 | 94.9 | 93.2 | 85.2 |
| secondary alcohol (relative GC %) | 0 | 0 | 0.1 | 0.2 | 0.4 | 0.6 | 0.8 | 0.9 |
| primary vs. secondary alcohol formation selectivity (%) | | 100 | 99 | 99.4 | 99.1 | 98.8 | 98.4 | 98.2 |

*hydrogenation of alkyne observed as the major competitive reaction.
Note:
primary vs. secondary alcohol selectivity (%) = 100 × (% primary alcohol − % secondary alcohol)/(% primary alcohol + % secondary alcohol).

| | t (h) | | | | | | |
|---|---|---|---|---|---|---|---|
| | 0 | 0.5 | 1 | 2 | 3 | 5 | 7 |
| Aldehydic substrate (relative GC %) | 100 | 68 | 48 | 22 | 11 | 2.5 | 0 |
| Ketonic substrate (relative GC %) | 100 | 99.9 | 99.7 | 99.5 | 99 | 98.6 | 97.9 |
| primary vs. secondary alcohol formation selectivity (%)* | | 99.1 | 98.9 | 98.7 | 97.8 | 97.2 | 95.9 |

*no hydrogenation of alkenes observed.
Note:
primary vs. secondary alcohol selectivity (%) = 100 × (% primary alcohol − % secondary alcohol)/(% primary alcohol + % secondary alcohol).

What is claimed is:
1. A process for the reduction by hydrogenation, using molecular $H_2$, of a $C_5$-$C_{20}$ substrate of formula

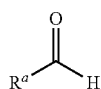

(I)

wherein $R^a$ represents a $C_4$-$C_{19}$ linear, branched or cyclic alkyl, alkenyl or alkadienyl group optionally comprising an aromatic ring and optionally comprising one, two or three functional groups selected among ketone, ether, carbon-carbon double or triple bond and carboxylic groups; into the corresponding alcohol or diol, characterized in that said process is carried out in the presence of at least one complex of formula

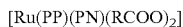  (1)

wherein PP represents a $C_6$-$C_{50}$ bidentate ligand of formula

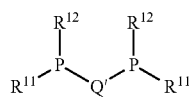  (C)

wherein $R^{11}$ and $R^{12}$, when taken separately, represent, simultaneously or independently, a $C_{3-6}$ branched or cyclic alkyl group or a $C_{6-10}$ aromatic group optionally substituted; and Q' represents a group of formula

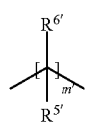  (i')

wherein m' is 1, 2, 3 or 4 and
$R^{5'}$ and $R^{6'}$ represent, simultaneously or independently, a hydrogen atom, a $C_{1-6}$ linear or branched alkyl group or a $C_{6-10}$ aromatic group optionally substituted; two distinct $R^{6'}$ and/or $R^{5'}$ groups, taken together, may form a $C_3$ to $C_8$ saturated or unsaturated ring optionally substituted, including the atoms to which said $R^{6'}$ and/or $R^{5'}$ groups are bonded, and optionally containing one or two additional nitrogen or oxygen atoms; or
a $C_{10}$-$C_{16}$ metallocenediyl, a 2,2'-diphenyl, a 1,1'-binaphthalene-2,2'-diyl, a benzenediyl, a naphthalenediyl, 2,3-bicyclo[2:2:1]hept-5-enediyl, 4,6-phenoxazinediyl, 4,5-(9,9-dimethyl)-xanthenediyl, or bis(phen-2-yl)ether group optionally substituted;
PN represents a $C_2$-$C_{20}$ bidentate ligand of formula

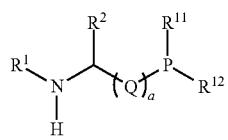  (B)

wherein a represent 0 or 1, $R^{11}$ and $R^{12}$ being defined as for PP;
$R^1$ represent, simultaneously or independently, a hydrogen atom or a $C_{1-6}$ linear, branched or cyclic alkyl group or a benzyl group optionally substituted;
$R^2$ represents a hydrogen atom, a $C_{1-6}$ linear, branched alkyl group or a $C_{6-10}$ aromatic group optionally substituted; $R^1$ and $R^2$, taken together, may form a saturated heterocycle containing 5 to 8 atoms and including the atoms to which said $R^1$ and $R^2$ are bonded, and optionally containing one additional nitrogen or oxygen atom; and Q represents a group of formula

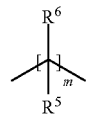  (i)

wherein m is 1, 2 or 3, and
$R^5$ and $R^6$ represent, simultaneously or independently, a hydrogen atom, a $C_{1-6}$ linear, branched or cyclic alkyl or, a $C_{6-10}$ aromatic group optionally substituted; two distinct $R^6$ and/or $R^5$ groups, taken together, may form a $C_{3-8}$ saturated ring optionally substituted, including the atoms to which said $R^6$ and/or $R^5$, groups are bonded, and optionally containing one or two additional nitrogen or oxygen atoms; or
a $C_{10}$-$C_{16}$ metallocenediyl group, a benzenediyl group, or a naphthalenediyl group, said group being optionally substituted;
the optional substituents of $R^{5'}$, $R^{6'}$, $R^{11}$ and $R^{12}$ are one to five halogen atoms (in particular when said substituents are on aromatic moieties), or one, two or three i) $C_{1-6}$ linear or branched alkyl alkoxy, groups or halo- or perhalo-hydrocarbon, amine groups, ii) $COOR^h$ wherein $R^h$ is a $C_{1-6}$ linear, branched or cyclic alkyl group, iii) $NO_2$ group, or iv) a benzyl group or a fused or non-fused phenyl group, said group being optionally substituted by one, two or three halogen atoms, $C_{1-8}$ alkyl, alkoxy, amino, nitro, ester, sulfonate or halo- or perhalo-hydrocarbon groups; and
each R represents, simultaneously or independently, a $C_2$-$C_{12}$ hydrocarbon group branched or cyclic in the α and/or β position, and said hydrocarbon group is optionally comprising one to five heteroatom selected amongst halogen, oxygen and nitrogen atoms; and
optionally an acidic additive.

2. A process according to claim 1, characterised in that each R represents, simultaneously or independently:
a $C_{2-12}$ alkyl group branched or cyclic in the α and/or β position
optionally substituted by one phenyl group optionally substituted by one to five halogen atoms and/or by $C_{1-4}$ alkyl or alkoxyl groups; and
optionally comprising one OH, amino or ether functional group;
or
a phenyl group optionally substituted by one to three, or live, halogen atoms and/or by $C_{1-4}$ alkyl or alkoxyl groups and/or by nitro groups.

3. A process according to claim 1, characterised in that the bidentate PN ligand is a compound of formula

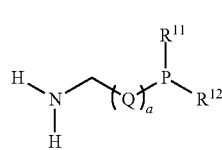  (B')

wherein a represents 0 or 1, $R^{11}$ and $R^{12}$ being defined in claim 1; and Q represents
a group of forms

(i)

wherein in is 1 or 2, and $R^6$ represents, simultaneously or independently, a hydrogen atom, a $C_{1-4}$ linear or branched alkyl group; or a benzenediyl group optionally substituted.

4. A process according to claim 1, characterised in that each $R^{11}$ and $R^{12}$ represent each, simultaneously or independently, a $C_{4-6}$ branched or cyclic alkyl group or a phenyl group optionally substituted.

5. A process according to claim 1, characterised in that said PP ligand is a compound of formula (C) wherein $R^{11}$ and $R^{12}$ represent, simultaneously or independently, a $C_{4-6}$ branched or cyclic alkyl group or a phenyl group optionally substituted; and Q' represents a $C_1$-$C_4$ alkanediyl radical optionally substituted, a $C_{10}$-$C_{12}$ ferrocenediyl, a 2,2'-diphenyl, a 1,2-benzenediyl or a naphthalenediyl group.

6. A process according to claim 1, characterised in that said acidic additive may be selected amongst the weak protic acids having a $pK_a$ comprised between 2 and 11.

7. A process according to claim 1, characterised in that acidic; additive is selected amongst:
a carboxylic acid of formula RCOOH, wherein R is as defined above in formula (1); and
phenol ($C_6H_5OH$) and a phenol substituted by one or two, or up to five, halogen atoms and/or $C_{1-4}$ alkyl or alkoxyl groups and/or nitro groups and/or carboalkoxy groups.

8. A ruthenium complex of formula

[RU(PP)(PN)(RCOO)$_2$]  (1)

as defined in claim 1.

9. The ruthenium complex of claim 8 wherein the hydrocarbon group of R comprises one to five heteroatoms selected amongst halogen, oxygen and nitrogen atoms.

10. The process of claim 1 wherein the hydrocarbon group of R comprises one to five heteroatoms selected amongst halogen, oxygen and nitrogen atoms.

* * * * *

UNITED STATES PATENT AND TRADEMARK OFFICE
CERTIFICATE OF CORRECTION

PATENT NO. : 9,714,263 B2
APPLICATION NO. : 14/777502
DATED : July 25, 2017
INVENTOR(S) : Dupau et al.

Page 1 of 1

It is certified that error appears in the above-identified patent and that said Letters Patent is hereby corrected as shown below:

In the Claims

Column 38:
Line 54, Claim 2; before "halogen atoms", delete "live" and insert -- five --.

Column 39:
Line 12, Claim 3; before "is 1 or 2, and", delete "in" and insert -- m --.

Column 40:
Line 8, Claim 7; before "additive is selected amongst:", delete "acidic;" and insert -- acidic --.

Signed and Sealed this
Fifth Day of September, 2017

Joseph Matal
*Performing the Functions and Duties of the
Under Secretary of Commerce for Intellectual Property and
Director of the United States Patent and Trademark Office*